(12) United States Patent
Murphy

(10) Patent No.: US 7,053,194 B2
(45) Date of Patent: May 30, 2006

(54) COMPOSITIONS AND METHODS FOR P53-MEDIATED REPRESSION OF GENE EXPRESSION

(75) Inventor: Maureen Murphy, Philadelphia, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 449 days.

(21) Appl. No.: 10/108,877

(22) Filed: Mar. 28, 2002

(65) Prior Publication Data

US 2003/0083482 A1    May 1, 2003

Related U.S. Application Data

(63) Continuation-in-part of application No. PCT/US00/27078, filed on Oct. 2, 2000.

(60) Provisional application No. 60/157,171, filed on Sep. 30, 1999, now abandoned.

(51) Int. Cl.
*C07H 21/04*    (2006.01)
*C12N 15/09*    (2006.01)

(52) U.S. Cl. .................................... 536/23.1; 435/320.1
(58) Field of Classification Search ............... 536/23.1; 435/320.1
See application file for complete search history.

(56) References Cited

OTHER PUBLICATIONS

Bao, R. et al. "Activation of Cancer-Specific Gene Expression by the Survivin Promoter"; Journal of the National Cancer Institute, 94(7): 522-528 (2002).

Hoffman, W.H. et al. "Transcriptional Repression of the Anti-apoptotic *survivin* Gene by Wild Type p53", 277(5): 3247-3257 (2002).

Yang, L. et al. "Tumor-specific gene expression using the survivin promoter is further increased by hypoxia"; Gene Therapy, 11: 1215-1233 (2004).

*Primary Examiner*—James Ketter
*Assistant Examiner*—Tara L. Garvey
(74) *Attorney, Agent, or Firm*—Dann Dorfman Herrell & Skillman; Kathleen D. Rigaut

(57) ABSTRACT

Compositions and methods are provided for identifying novel therapeutic agents for the treatment of cancer and other cellular proliferative disorders.

36 Claims, 9 Drawing Sheets

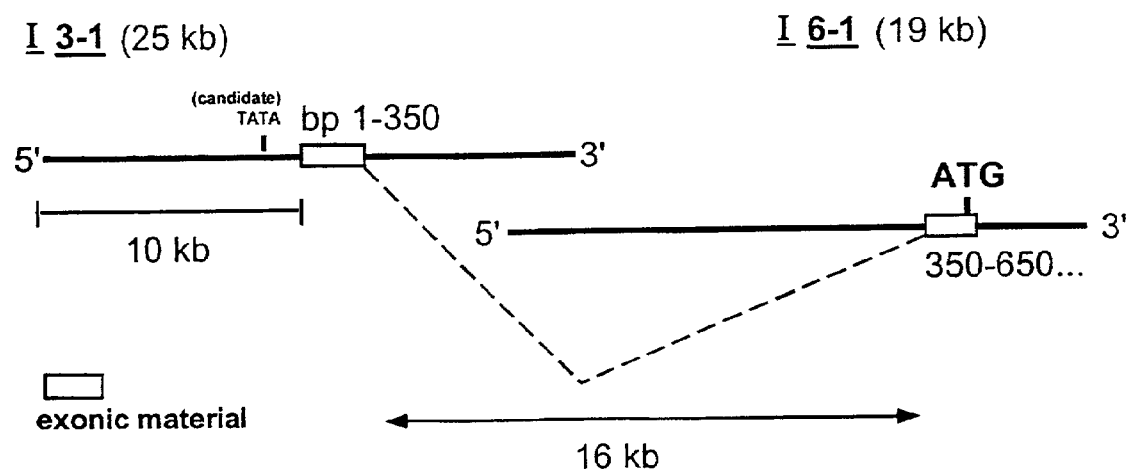
Figure 1: Map4 Genomic Structure

Fig. 2A
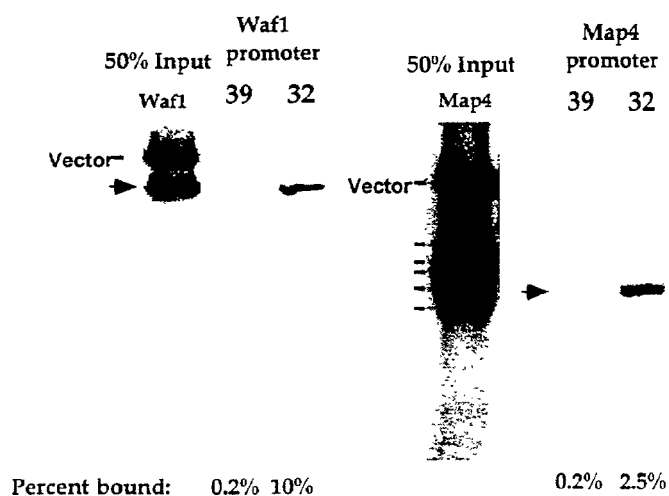
Map4 promoter structure (Xba I fragments)
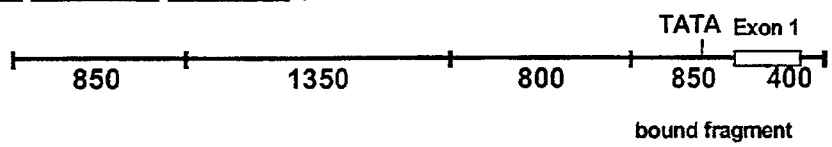
Fig. 2B
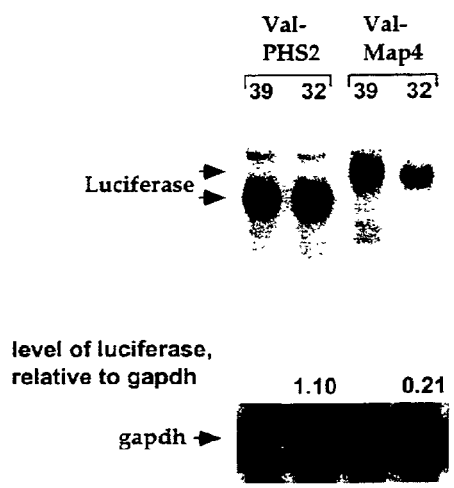

Fig. 4E  Flow Cytometry Data

|  | 39 | | | 32 (wild type) | | |
|---|---|---|---|---|---|---|
|  | G1 | S | G2/M | G1 | S | G2/M |
| H1299 ts p53 | 46 | 34 | 20 | 62 | 8 | 30 |
| H1299 ts p73b | 42 | 27 | 31 | 68 | 8 | 24 |

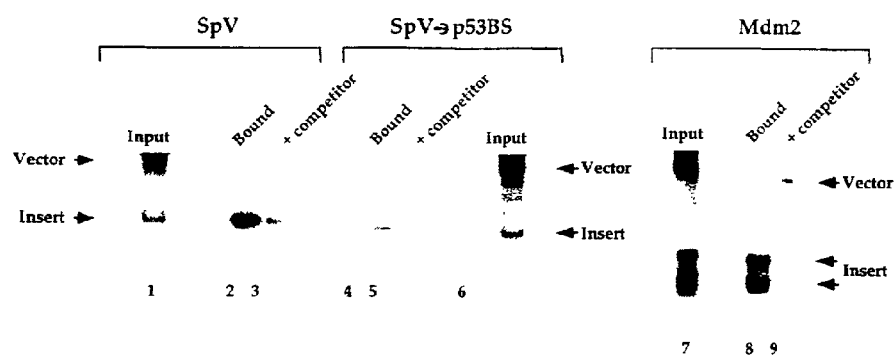
Fig. 7A
Fig. 7B
Fig. 7C Sequence of the p53-repressing element of the survivn promoter
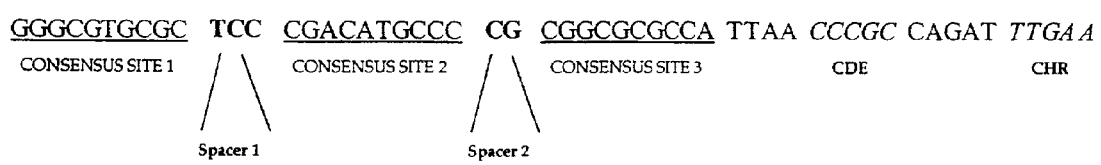

COMPOSITIONS AND METHODS FOR P53-MEDIATED REPRESSION OF GENE EXPRESSION

This application is a continuation-in-part of PCT/US00/27078 filed Oct. 2, 2000 which in turn claims priority under 35 U.S.C. §119(e) to U.S. Provisional Application 60/157,171, filed Sep. 30, 1999, now abandoned.

Pursuant to 35 U.S.C. §202(c), it is acknowledged that the U.S. Government has certain rights in the invention described herein which was made in part with funds from the National Institutes of Health.

FIELD OF THE INVENTION

This invention relates to diagnosis and treatment of neoplastic diseases. More specifically, this invention provides novel nucleic acid molecules and proteins involved in p53-mediated repression of gene expression.

BACKGROUND OF THE INVENTION

Several publications and patent documents are referenced in this application to more fully describe the state of the art to which this invention pertains. The disclosure of each of these publications is incorporated by reference herein.

The p53 tumor suppressor protein is a nuclear phosphoprotein that functions in cell-cycle arrest, programmed cell death (apoptosis), inhibition of tumor growth, and preservation of genetic stability. The p53 gene is inactivated by mutation in over 60% of human tumor samples analyzed. This gene continues to hold distinction as the most frequently mutated gene in human cancer. The strong selection for mutation of p53 in cancer cells can be explained by the normal functions of the protein. p53 protein is normally expressed at very low levels in cells and is latent in activity. The protein is post translationally stabilized and activated as a transcription factor by a number of stimuli that are detrimental to the normal cell, notably genotoxic stress, hypoxia, and the mutational activation of oncogenes like c-myc and Ha-ras. The result of p53 induction in a cell is either growth arrest in the G1 phase of the cell cycle, or programmed cell death (apoptosis). The choice of fate depends upon a number of factors, including cell type, level of p53 induced, and environmental factors, such as the presence of cytokines or increased expression of bcl2 family members. It is currently accepted that it is the ability of p53 to induce cell death, not G1 growth arrest, that underlies the powerful selection for mutation of the p53 gene in tumorigenesis.

The best-understood activity of p53 remains its ability to function as a sequence-specific transcriptional activator. Following a stimulus such as DNA damage, p53 protein is post-translationally stabilized and activated for DNA binding. This protein then binds in a sequence-specific manner to promoters or enhancers containing the consensus element 5' Pu Pu Pu C A/T T/A G Py Py Py 3'. (SEQ ID NO: 12) p53 binding to these elements is believed to recruit the core transcriptional apparatus and thereby enhance the transcription of such (p53-response) genes.

Despite the ability of p53 to transactivate pro-apoptotic genes like bax and IGF-BP3, in the past several years compelling indications have accumulated that p53 has a pro-apoptotic activity that is independent of its transactivation function. Recently it has been shown that physiological induction of wt p53 can lead to apoptosis in the absence of trans-activation of p53 response genes.

In addition to its well-characterized function as a transcriptional activator, p53 has a poorly-understood activity as a transcriptional repressor. Previous studies investigating this function of p53 were performed using transient over-expression assays where non-physiological levels of p53 and candidate promoters are introduced into cells. In this type of setting, a large number of promoters are repressed by p53. In no case, however, have these endogenous genes been found to be repressed by p53. Therefore, in these types of assays, transcriptional repression by p53 is non-physiological, and impossible to distinguish from transcriptional "squelching". During transcriptional "squelching", a powerful transactivator like p53 represses transcription of other promoters non-specifically by more efficiently recruiting basal transcription factors, such as TBP-associated factors (TAFs).

To determine whether p53 can function as a sequence-specific transcriptional repressor, differences in gene expression in cells containing an inducible p53 protein have been analyzed (Murphy et al., Genes & Devel. 10:2971–2980, 1996). Several genes were identified that exhibit decreased expression following wt p53 induction in cell lines containing a well-characterized temperature-sensitive mutant of p53. One of these genes encodes the microtubule-associated protein Map4. It was found that p53 induction leads to repression of Map4 at the level of transcriptional initiation (Murphy et al., Genes & Devel. 10:2971–2980, 1996). This transcriptional repression is manifested at both the RNA and protein levels, and approaches a 90% reduction at the RNA level following p53 induction for 24 hours. Further, physiological induction of p53, by DNA damaging agents or ionizing radiation, leads to significant repression of Map4 in both normal and tumor cells containing wt p53. In cells with mutant p53, Map4 levels are unaffected by such treatments (Murphy et al., Genes & Devel. 10:2971–2980, 1996). This and other data indicate that independent of it's cell cycle effects, wt p53 represses the expression of Map4. However, the precise mechanism by which p53 represses Map4 expression remains to be elucidated.

The Map4 gene is transcriptionally repressed following p53 induction in cells that undergo either G1 arrest or apoptosis in response to p53. Significantly, it has been found that removing Map4 from transcriptional repression by p53 significantly interferes with p53 dependent apoptosis (Murphy et al., Genes & Devel. 10:2971–2980, 1996), thereby directly placing Map4 in a pathway influential in p53-mediated programmed cell death.

Following the cloning of Map4 as the first endogenous gene repressed by physiological induction of wt p53, several other genes have been cloned that exhibit decreased expression following p53 induction. These genes include those encoding DNA topoisomerase IIα, wee1, DP-1, presenilin 1, and others. It is clear from these studies that there will exist other candidate p53-repressed genes. Significantly, repression of at least one of these genes, presenilin 1, has been demonstrated to contribute to the progression of apoptosis. Further, the combined data from several sources suggest a perfect correlation between the ability of p53 to induce apoptosis, and its ability to repress the expression of genes like Map4.

It is clear from the foregoing that the expression repression function of p53 is a significant part of p53's central role in controlling cell growth and death. In order to utilize this function in a practical way, more information is needed relative to the physical interactions among p53 and its targets for repression in cells.

SUMMARY OF THE INVENTION

In one embodiment of the invention isolated nucleic acid molecules comprising promoter regions containing p53 negative response elements having a sequence of SEQ ID NOS:1, 2 or 3 are provided. Expression vectors comprising the promoter sequences described herein operably linked to a heterologous nucleic acid molecule are also within the scope of the present invention. In a preferred embodiment of the invention, the heterologous nucleic acid molecule encodes a reporter gene. Reporter genes suitable for this purpose include, without limitation, β-galactosidase, chloramphenicol acetyltransferase, luciferase, secreted alkaline phosphatase and green fluorescent protein.

In yet a further aspect of the invention, an isolated host cell transformed with the expression vector described above is provided. Host cells contemplated for use in this aspect of the invention include procaryotic, eucaryotic, fungal, plant, mammalian and insect cells.

In a further aspect of the invention a process for producing a host cell containing a heterologous gene operably linked to the survivin or Map4 promoter is provided. The process comprises i) transfecting a cell with an expression vector comprising a heterologous gene operably linked to the promoter, the expression vector optionally containing a selectable marker gene; and ii) selecting and isolating transformed host cells. In this embodiment of the invention, the selectable marker gene may or may not be on the same expression construct as the promoter/reporter gene construct. Additionally, the promoter sequence utilized may be the native promoter sequence or one or more of the minimal p53 repressor elements (SEQ ID NO:3) described herein. In the broadest aspect of this embodiment, the invention encompasses the use of the following site and any permutations thereof, either in whole or in part, as a p53-repressing element: Pu Pu Pu C A/T T/A G Py Py Py N (0–13) Pu Pu Pu C A/T T/A G Py Py Py N (0–15) G/C G C G G N (5–6) T T G A A (SEQ ID NO: 13) where N is any nucleotide, Pu is a purine, Py is a pyrimidine, and the slash marks such as G/C means G or C. N (0–13) means between 0 to 13 nucleotides of any sequence. This consensus may have as many as 5 mismatches and should continue to function as a repressing element.

Methods utilizing the expression constructs and host cells containing the same for identifying agents which affect the promoter activity of the Map4 or survivin gene are also provided in the present invention. Transformed host cells are contacted with an agent which inhibit or stimulate promoter activity. Influence of the test agent on promoter function is determined based on levels of expression of the reporter gene relative to the appropriate negative controls.

In yet a further aspect of the invention, methods are provided for screening the Map4 and survivin promoter for mutations associated with pathological conditions. Mutational analysis is well known in the art and can be performed by hybridizing a sequence having the sequence of SEQ ID NOS: 1, 2 or 3 with the corresponding promoter sequence from a patient. Many systems are currently available for detecting the presence of deletions, insertions and mismatches between such nucleic acid duplexes.

Another aspect of the invention provides a method for selectively targeting p53 dysfunctional tumor cells for destruction, while sparing normal cells. The method comprises administering to a patient a DNA construct comprising the aforementioned DNA segment operably linked to a coding sequence which, upon expression, produces a product that renders the cell a target for destruction by an exogenous agent. This gene will be expressed in p53 defective tumor cells, but not in normal cells. The patient is then treated with the exogenous agent, resulting in the selective destruction of the p53-defective tumor cells while sparing normal cells.

Other features and advantages of the present invention will become apparent by reference to the drawings, detailed description and examples that follow.

BRIEF DESCRIPTION OF THE DRAWINGS

FIG. 1. Map4 genomic structure. Two contiguous phage clones isolated from a library screen using the first 650 basepairs (bp) of the Map4 cDNA were mapped by restriction digestion and sub-cloning. The first 650 nucleotides of the published murine Map4 cDNA were found to reside on two exons of this gene. The putative first exon is completely non-coding, while the second exon (bp 350 to 650 and further) contains the start site for translation (ATG). 150 nucleotides upstream from the first nucleotide of the Map4 cDNA is a potential TATA box. All fragments of phage 3-1, including 10 kb of potential promoter region, have been subcloned.

FIGS. 2A–2B. Autoradiogram and diagram showing a specific fragment of the Map4 promoter retained by p53 in an in vivo binding assay. A specific fragment of the Map4 promoter is immunoprecipitated with p53 from whole-cell extract from Va15 (ts p53) cells grown at 32 degrees (wt p53). The diagram of the Map4 promoter (below) indicates that the 850 base pair containing the putative TATA box is specifically retained by p53 in this assay (FIG. 2A).

FIG. 2B shows Northern analysis of luciferase mRNA levels in pooled, stable transfectants of Va15 cells (wild type p53 at 32 degrees) containing the luciferase gene linked to either the PHS-2 promoter (negative control) or the Map4 promoter. Ratios given are the levels of luciferase RNA at 32 degrees compared to 39 degrees, relative to the housekeeping gene glyceraldehyde 6-phosphate dehydrogenase.

FIG. 3A depicts a western blot showing that p53 induction in human MCF7 breast carcinoma cells leads to down-regulation of survivin protein. FIG. 3B shows the results of immunopreciptation assays showing that cyclin-dependent kinase assays indicate that MCF7 cells treated with doxorubicin arrest in G2/M phase, where survivin expression is normally high. FIG. 3C is a blot showing that cells arrested in G2/M with nocodazole maintain the ability to down-regulate survivin following induction of p53 by temperature shift.

FIGS. 4A–4E. FIG. 4A shows a northern which reveals that survivin is down-regulated at the RNA level following p53 induction. FIG. 4B shows the results of western analysis revealing that survivin down regulation requires the presence of wild type p53. FIG. 4C is a western blot showing that the human papillomavirus E6 protein, which targets p53 for degradation, is sufficient to inhibit doxorubicin-mediated down-regulation of survivin. FIG. 4D is a northern blot showing that inducible p53, but not p73β, negatively regulates survivin gene expression.

FIG. 4E shows the results of flow cytometry analysis of H1299 ts-p53 and ts p73 cells indicating that both cell types arrest at G1 and G2/M at 32°.

Figure 6A:
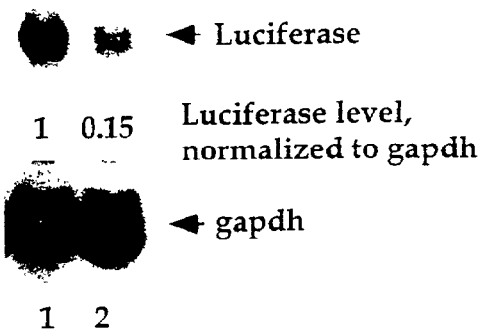
Figure 6B:
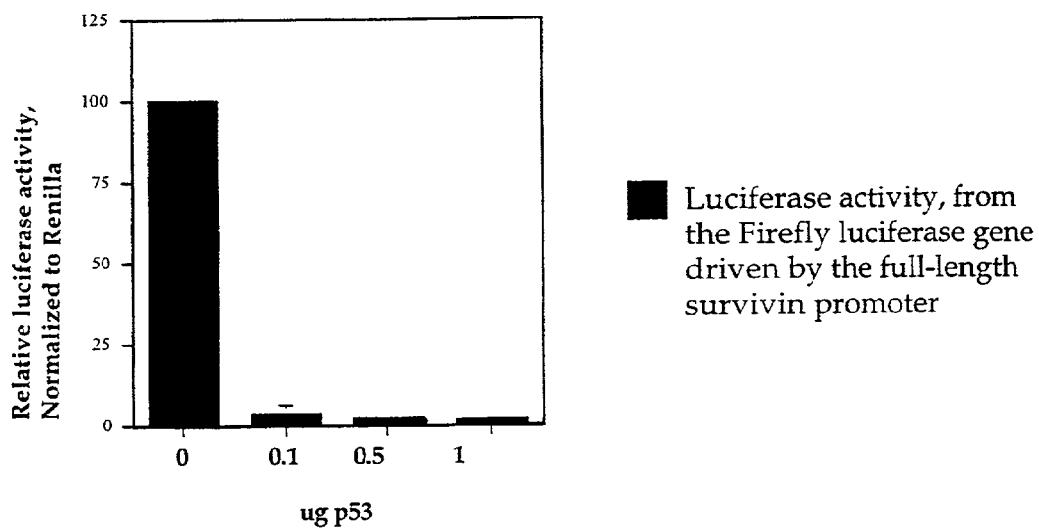

FIGS. 6A–6B FIG. 6A is a northern blot showing that the survivin promoter is sufficient to confer negative regulation of the firefly luciferase gene by p53.

FIG. 6B shows the combined data from luciferase assays from cells transfected with the survivin promoter driving the luciferase gene, along with increasing amounts of p53. These data were normalized to a co-transfected luciferase gene, which uses a unique and different substrate (Renilla luciferase), and which is driven by the immediate-early cytomegalovirus promoter.

FIGS. 7A–7C. FIG. 7A shows an immunobinding assay revealing that cells containing p53 (lane 3) specifically immunoprecipitate the survivin promoter, but cells that have no p53 (lane 2) do not bind to this element. FIG. 7B shows the same assay, but also shows that addition of excess unlabeled survivin promoter can compete away this binding (lane 3), indicating that this binding is sequencespecific. Additionally, deletion of the p53 binding site in this promoter abolishes binding of p53 to the survivin promoter (lane 4). FIG. 7C shows the nucleotide sequence (SEQ ID NO: 3) of the element in the survivin promoter that binds to p53; the ten base pair consensus sites for p53 are underlined, and the spacer elements, which are not present in the p53 binding sites of trans-activated genes, are shown in bold. Also delineated by italics are the CDE and CHR elements, which are found in many genes that, like survivin, are highly expressed in G2/M.

Figure 8A:
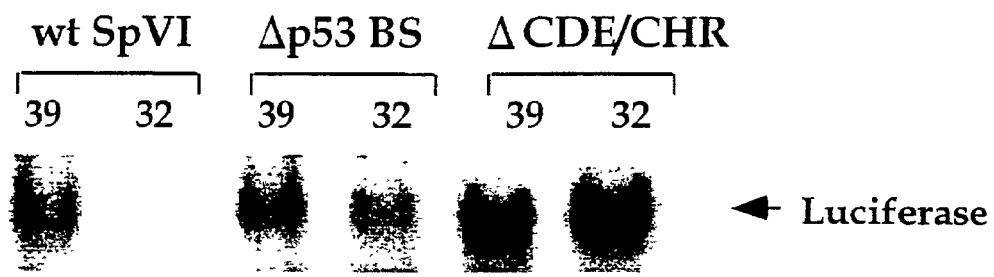
Figure 8B:
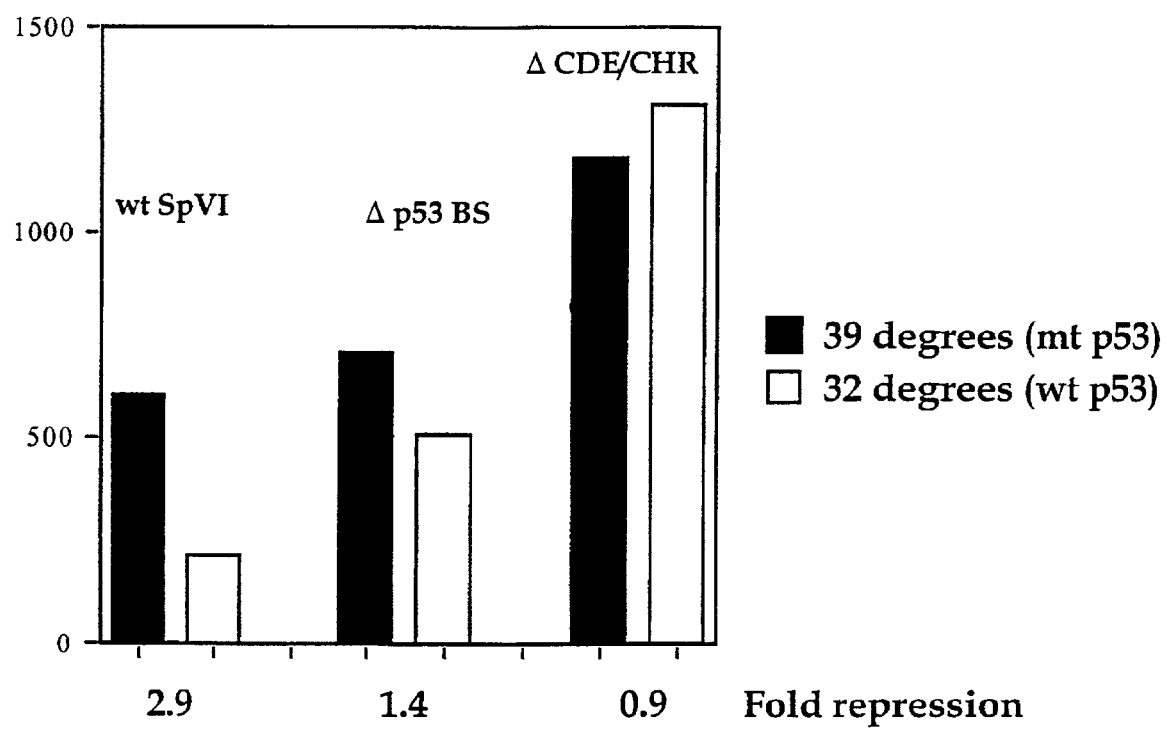
Figure 8C:
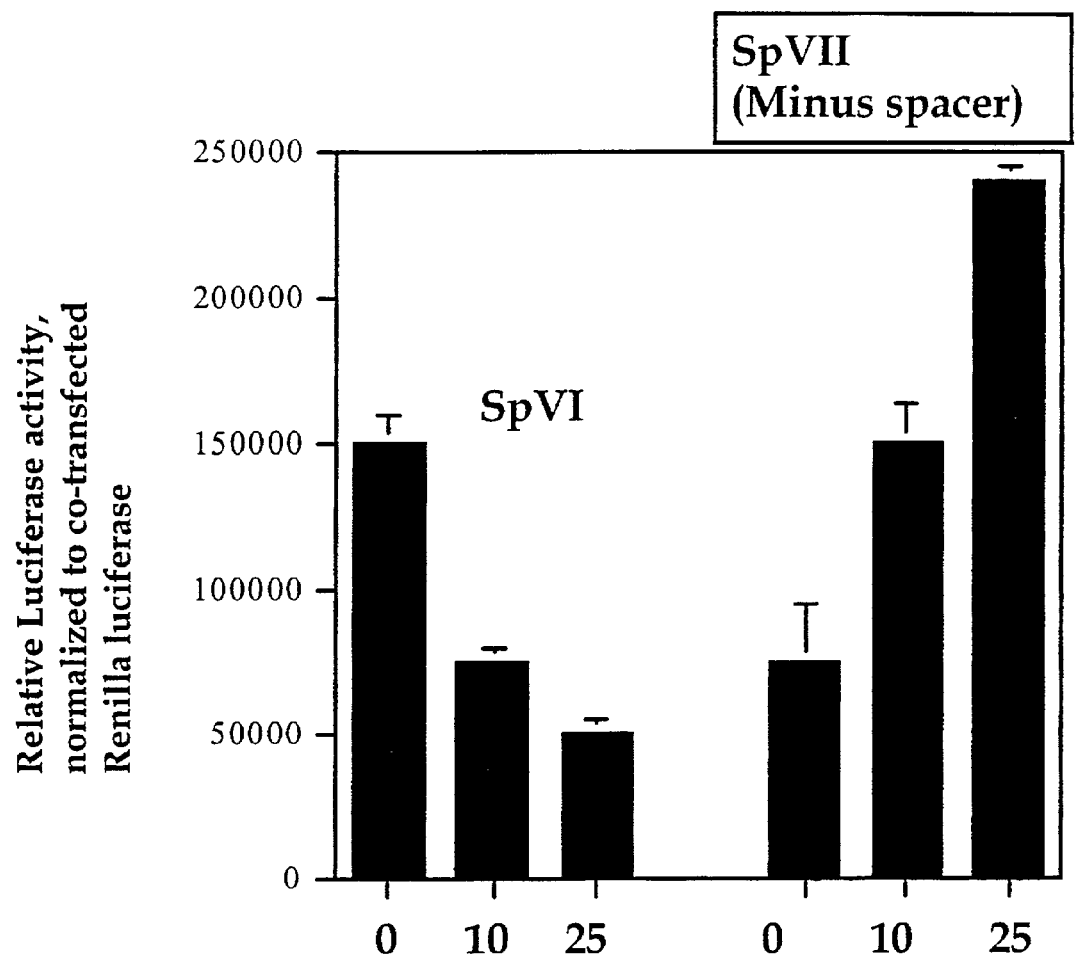

FIGS. 8A–8C. FIG. 8A shows the results of Northern analysis of the minimal p53-repressing element (depicted in FIG. 7C.) linked to the luciferase reporter gene, in the presence of mutant (first lane) and wild type (second lane, 32 degrees) p53. Deletion of the three ten-base-pair p53 consensus sequences in the element impairs the ability of p53 to repress this promoter (lanes 3 and 4). Additionally, deletion of the CDE/CHR element, renders p53 unable to repress the linked luciferase gene (lanes 5 and 6). FIG. 8B shows quantitation of the level of luciferase mRNA in each lane in FIG. 8A, normalized to the level of the housekeeping gene, glyceraldehyde 6-phosphate dehydrogenase. FIG. 8C shows a comparison of the ability of p53 to repress a minimal promoter containing the p53-binding site of survivin, versus the same element wherein the 3 bp TCC spacer has been deleted, when both elements are individually linked to the firefly luciferase reporter gene and luciferase activity is monitored.

DETAILED DESCRIPTION OF THE INVENTION

I. Definitions:

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived.

For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

Nucleic acid sequences and amino acid sequences can be compared using computer programs that align the similar sequences of the nucleic or amino acids thus define the differences. As one example, the CLUSTLW program and parameters employed therein may be utilized (Thompson et al., 1994, supra). However, equivalent alignments and similarity/identity assessments can be obtained through the use of any standard alignment software. For instance, the BLAST programs used to query sequence similarity in GenBank and other public databases may be used. The GCG Wisconsin Package version 9.1, available from the Genetics Computer Group in Madison, Wisconsin, and the default parameters used (gap creation penalty=12, gap extension penalty=4) by that program may also be used to compare sequence identity and similarity.

The term "substantially the same" refers to nucleic acid or amino acid sequences having sequence variation that do not materially affect the nature of the protein (i.e. the structure, stability characteristics, substrate specificity and/or biological activity of the protein).

With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program. In an exemplary embodiment of the invention, the Smith-Waterman algorithm is used to determine percent similarity and percent identity among protein sequences.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to oligonucleotides or other single-stranded nucleic acid molecules, the term "specifically hybridizing" refers to the association between two single stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression vector. Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell. The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "clone" is a population of cells derived from a single cell or common ancestor by mitosis.

A "cell line" is a clone of a primary cell that is capable of stable growth in vitro for many generations.

II. Description

In accordance with the present invention, several discoveries have been made in connection with the repressor function of p53 in cells. The result of these discoveries is the identification of novel biological molecules and targets for drug development, to control gene expression and cell proliferation. Significantly, the present inventor has identified:

1. Novel DNA repressor elements that confer negative regulation by the p53 tumor suppressor protein;

2. a newly-discovered mechanism of transcriptional repression, involving physical interaction between p53, mSin3a and histone deacetylases; and 3. Negative repression of the anti-apoptotic survivin promoter under p53 inducing conditions.

Each of these inventive aspects is described below.

A. Sequences from the Map4 Promoter are Sufficient to Confer p53-Mediated Negative Regulation to a Heterologous Gene Integrated into Chromatin.

A DNA construct was assembled, comprising 4.3 kilobases of DNA of the upstream Map4 region operably linked to a promoterless luciferase reporter gene. It was found that expression of luciferase is decreased following p53 induction in the Map4-promoter transfectants, but not in stable transfectants of luciferase driven by the PHS-2 (prostaglandin synthetase-2) promoter, which is not regulated by p53. These experiments are described in greater detail in Example 1.

Also as described in Example 1, a region of the Map4 promoter that specifically-binds p53 has been localized to an 850 bp XbaI fragment in the promoter region. The location of the fragment is shown in FIG. 2. A portion of the promoter containing the 850 bp p53-binding fragment is set forth herein as SEQ ID NO:1. Referring to this sequence, the 850 bp fragment is located at bases 1900–2690. The transcription start site of the Map4 gene is located at approximately base 2531, and the first exon resides between bases 2531 and 3020.

It is believed that the Map4 promoter region contains the first DNA sequence element shown to confer transcriptional repression by p53, even when stably integrated into chromatin. Therefore, this promoter, with its p53 negative response element (NRE) will be of significant practical utility as a transcriptional control element for gene therapy constructs designed to selectively target tumor cells that contain mutant or inactivated p53 protein, while at the same time sparing normal cells.

The present inventors have also identified a sequence element present in the survivin promoter, which when bound by p53 also results in repression of survivin expression. Survivin is a well-known potent inhibitor of apoptosis. Several studies have suggested that during tumorigenesis, survivin appears to be reactivated, thereby promoting tumor cell survival by inhibiting the cell death pathway. The identification of this p53 repressible element in the survivin promoter facilitates the development of compositions and methods useful for identifying therapeutic agents which affect this pathway.

As one example of a DNA construct for such a therapeutic application, the expression of the herpes simplex virus thymidine kinase (HSV-TK) gene, whose expression is toxic in the presence of the drug gancyclovir, could be driven by promoter containing the p53 repressible sequence elements of the invention. Only tumor cells with inactive p53 would express the TK gene and be susceptible to killing by gancyclovir treatment. At the same time, normal cells would be spared. Over 60% of human tumors mutate and inactivate p53. Furthermore, over 98% of human cervical carcinomas associated with human papillomavirus infection show greatly decreased expression of p53, due to expression of the HPV E6 gene, which targets p53 for degradation.

Constructs such as the one described above, which utilize the Map4 or the survivin promoter to selectively target p53 mutated tumor cells for destruction, will be of utility in treatment of many types of tumors.

The p53 NRE of the Map4 and survivin promoters also provides utility in tumor-targeted gene therapies that employ viral vectors for gene delivery. In many cases, it is desirable that the virus and its contents replicate in tumor cells, but not in normal cells, since expression of viral genes in normal cells can lead to viral takeover of those cells. Accordingly, a viral gene therapy vehicle (e.g., an adenovirus vector) can be constructed such that selected viral vectors are controlled by the Map4 or survivin promoters containing the p53 negative response element of the invention. In p53-defective tumor cells, viral genes and the therapeutic genes will be expressed, while in normal cells (i.e., those containing functional p53), viral gene expression will be repressed.

In another approach, gene therapy may involve expression of an antisense mRNA driven by the p53 repressible element. In this embodiment, the p53 repressible element (or a plurality of the same) would be operably linked to an antisense molecule specific for a protein essential for tumor cell life, (e.g., bcl–2, survivin, P-glycoprotein). Expression of such an antisense molecule in cells lacking p53 would inhibit expression of the essential tumor cell gene, thereby killing the targeted tumor cell.

B. P53 Interacts in vivo with the Co-repressor Sin3

Several proteins that are transcriptional repressors (e.g., Mad and pRB), have recently been found to exist in complexes with histone de-acetylases (HDACs). HDACs are enzymes that are responsible for locally removing acetyl groups from lysine residues on histones, and subsequently enhancing their affinity for DNA. This is believed to lead to chromatin condensation and subsequent transcriptional repression. To determine whether transcriptional repression via p53 might rely on HDAC activity, a reversible and specific inhibitor of HDACs, trichostatin A (TSA), was tested for its ability to inhibit the repression of genes negatively regulated by p53. These experiments are described in detail in Example 2.

Briefly, it was found that TSA abrogates the ability of p53 to repress the transcription of two genes that it negatively regulates, Map4 and stathmin. Consistent with this finding, the inventors also discovered that p53 physically associates in vivo with HDACs. This interaction is not direct, but rather is mediated by the co-repressor mSin3a. Both wt p53 and mSin3a, but not mutant p53, can be found bound to the Map4 promoter at times when this promoter preferentially associates with de-acetylated histones in vivo. Significantly, inhibition of p53-mediated transcriptional repression with TSA markedly inhibits apoptosis induction by p53. These data offer the first mechanistic insights for p53-mediated transcriptional repression, and underscore the importance of this activity for apoptosis induction by p53.

The p53 and Sin3 interaction domains were mapped in vitro, using in vitro translated and GST-fusion proteins. The p53 domain from amino acids 1–160 is necessary and sufficient to bind to Sin3, while the paired amphipathic helix 3 (PAH3) domain of Sin3 mediates binding to p53.

The discoveries made in accordance with this aspect of the present invention can be utilized for a variety of purposes, including but not limited to (1) assay systems to identify pharmacological agents capable of suppressinq or enhancing cell proliferation by affecting the p53/Sin3-mediated transcription repression pathway described above; (2) diagnostic methods for assessing functional mutations in Sin3 and /or p53 relating to their ability to associate with each other or with HDACs or regulatory regions of other downstream targets involved in apoptosis; and (3) methods for controlling cell proliferation by regulating apoptosis via the p53/Sin3-mediated transcription repression pathway.

C. Transcriptional Repression of Survivin Gene Expression by Wild Type p53.

The survivin protein is a member of the IAP (inhibitor of apoptosis) family. This protein has potent anti-apoptotic activity, as well as an evolutionarily-conserved role as a mitotic spindle checkpoint protein. Previous studies on p53-repressed genes have implicated several components of microtubules, as well as microtubule-associated proteins, as targets of negative regulation by p53. While the transcriptional repression activity of p53 has been implicated in apoptosis induction by this protein, few targets of p53-repression have been identified that are anti-apoptotic. In a further embodiment of the invention, survivin has also been identified as a p53-repressed gene; this repression is shown to be distinct from induction of G1 arrest by p53. While p53 is capable of repressing the survivin promoter, the p53-homologue p73 is not. Immunobinding assays and chromatin immunoprecipitations indicate that p53 binds the survivin promoter at a site distinct from a canonical p53 response element, which consists of two pairs of palindromic pentamers separated by 0–1 base pairs. Instead the survivin site resembles those first identified for p53 by immunoselection protocols, containing a larger spacer between the pentamer pairs. Deletion of this spacer is sufficient to convert the survivin binding site from a repressing element into a trans-activating element. The results of this study are further described in Example 3.

D. Methods and Kits

According to another aspect of the invention, methods of screening drugs for therapy, i.e., promoting or inhibiting p53 mediated repression of target genes are provided.

The p53 repressible sequence elements may be employed in drug screening assays may either be free in solution, affixed to a solid support or within a cell. One method of drug screening utilizes eukaryotic or prokaryotic host cells which are stably transformed with recombinant polynucleotides expressing a p53 repressible sequence element containing promoter/reporter gene construct, preferably in competitive binding assays. Such cells, either in viable or fixed form, can be used for standard binding assays. One may determine, for example, formation of complexes between a Map4 or suvivin promoter and the agent being tested, or examine the degree to which the formation of a such a complex disrupts p53 binding to the sequence.

Another technique for drug screening provides high throughput screening for compounds having suitable binding affinity for the p53 repressible sequence elements or complexes containing the same and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with the p53 repressible sequence elements or complexes containing the same and bound polypeptide is then detected by methods well known in the art.

One goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19–21. In one approach, one first determines the three-dimensional structure of a protein of interest (e.g., p53 polypeptide) or, for example, of the p53-DNA-protein complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., Science 249:527–533, 1990). In addition, peptides (e.g., p53 polypeptide) may be analyzed by an alanine scan (Wells, Meth. Enzym. 202: 390–411, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have altered p53 activity or stability or which act as inhibitors, agonists, antagonists, etc. of p53 repressor functions. By virtue of the availability of cloned sequences, sufficient amounts of the p53 polypeptide may be made available to perform such analytical studies as x-ray crystallography.

In a particularly preferred embodiment of the invention, the promoter regions of the Map 4 or survivin genes are cloned upstream of a reporter gene. Reporter genes suitable for this purpose include, without limitation, beta galactosidase, luciferase, chloramphenicol acetyltransferase, and green fluorescent protein. Exemplary p53 repressible promoter sequence elements are set forth herein as SEQ ID NOS: 1,2 and 3.

Methods for operably linking the coding regions for the reporter genes to the promoter sequence elements of the invention are well known to those of ordinary skill in the art.

Following introduction of such DNA constructs into recipient host cells, the cells may be contacted with agents suspected of affecting p53 repressor activity. Agents capable of altering expression of the reporter gene may prove efficacious in regulating p53 action, thereby having therapeutic advantage in the treatment of cancer or other disorders where altered p53 expression plays a role.

E. Therapeutics

A. Pharmaceuticals and Peptide Therapies

The discovery that the expression of genes controlling apoptosis is altered in cancer and other proliferative disorders facilitates the development of pharmaceutical compositions useful for treatment and diagnosis of these syndromes and conditions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

F. Methods of Gene Therapy

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Gene transfer techniques which selectively target the p53 nucleic acid to affected tissues are preferred. Examples of this include receptor-mediated gene transfer, in which the nucleic acid is linked to a protein ligand via polylysine, with the ligand being specific for a receptor present on the surface of the target cells.

Several recently issued patents are directed to methods and compositions for performing gene therapy. See U.S. Pat. Nos. 6,168,916; 6,135,976; 5,965,541 and 6,129,705. Each of the foregoing patents is incorporated by reference herein.

According to another aspect of the invention, kits are provided to facilitate performing the above-described assays. In one embodiment, the kits comprise one or more DNA constructs encoding p53 fragments and mutants thereof, Sin3, HDACs, or downstream targets of p53-mediated repression, particularly and reporter genes operably linked to the Map4 or survin promoter negative response element, along with instructions on how to use the constructs to perform the assays of the invention. In another embodiment, the kits comprise aliquots of transgenic cells and instructions for their use. In another embodiment, the kits may comprise antibodies and other reagents for performing immunological assays. The kits may also comprise, optionally, various additional reagents for the assays, such as growth media, enzyme substrates for the reporter gene product, and standard solutions for calibrating expression of the reporter gene.

The following examples are provided to illustrate embodiments of the invention. They are not intended to limit the scope of the invention in any way.

EXAMPLE 1

Map4 Promoter Sequences that Confer p53-Mediated Negative Regulation of Gene Expression We screened a murine genomic library with Map4 sequences representing the first 650 nucleotides of the murine cDNA. Four positive genomic clones were isolated. Two of these genomic clones contained overlapping sequences (by hybridization analysis); rough maps of these are shown in FIG. 1. We cloned 4.3 kilobases of DNA of the upstream Map4 region into a promoterless luciferase reporter gene. This construct was stably-transfected into a well characterized murine cell line that contains a temperature-sensitive p53 protein (Va15 cells). In this cell line, p53 protein exists in a mutant conformation at 39° C., and temperature shift to 32° C. results in wt p53 protein, and G1 growth arrest. Several control promoters which are not repressed by p53 were cloned into the same luciferase vector and transfected identically. Over one hundred hygromycin resistant colonies from each transfection were pooled and expanded.

Total RNA was isolated from each cell line grown at 39° C. (mutant p53), and following temperature shift to 32° C. (wild type p53) for 24 hours. Northern analysis of this RNA with a luciferase probe was performed. (As we found that temperature-shift alone greatly enhanced luciferase activity in these lines, we were prompted to analyze RNA levels for luciferase instead of enzyme activity). Northern analysis revealed that the expression of luciferase is decreased following p53 induction in the Map4-promoter transfectants, but not in stable transfectants of luciferase driven by the PHS-2 (prostaglandin synthetase-2) promoter. Levels of the gapdh control likewise remain unchanged.

The slightly higher molecular weight luciferase transcript in the Map4-promoter transfectants results from the inclusion in this construct of approximately 350 base pairs of the Map4 cDNA (first published exon, 5' UTR). We have constructed a version of this construct that excludes this first exon, and is linked to the luciferase gene. This promoter construct is also negatively regulated by p53 in Va15 cells (not shown). Therefore, consistent with nuclear run-on experiments, mRNA elements from the Map4 gene appear to be dispensable for repression of this gene following p53 induction. This fragment of the Map4 promoter is the first piece of DNA identified that functions as a p53-negative regulatory element (p53-NRE) when integrated into chromatin.

We have also tested two independent single subclones of Map4-promoter/luciferase transfectants, and obtained identical results (luciferase mRNA expression is decreased following p53 induction). As other negative controls, we have used three other promoters linked to the luciferase gene; the SV40 promoter/enhancer, the CMV immediate early promoter, and the alpha-actin promoter. When stably-transfected into Va15 cells, these promoters are not repressed by wt p53 induction. Additionally, the Map4 luciferase construct is not repressed in cells that are null for p53 (10.1 cells, parental cells to Va15) following temperature shift to 32° C. (not shown).

We used an immuno-selection assay to test the hypothesis that p53 protein could physically interact with a region of the Map4 promoter. In this assay, as outlined by (Zauberman et al., Oncogene 10: 2361–2366, 1995), 200 ug of whole-cell extract from Va15 cells grown at 39° C. (mutant p53) or 32° C. (wt p53) is incubated with $10^5$ cpm of end labeled, restriction-digested plasmid containing the putative Map4 promoter, or a radio-labeled plasmid containing the p21/waf1 promoter (positive control). Radio-labeled DNA and extract are incubated in the presence of purified anti-p53 monoclonal antibodies and poly dI/dC as an inhibitor of non-specific DNA binding, followed by addition of protein A-sepharose. p53-immuno-complexes, containing p53 protein as well as bound DNA fragments, are pelleted with protein A sepharose, and these complexes are washed with binding buffer. Phenol-chloroform extraction of this reaction is followed by ethanol precipitation and loading of "bound" DNA (now liberated from protein) on a non-denaturing acrylamide gel.

As depicted in FIG. 2, a DNA fragment containing the waf1 promoter, known to contain two consensus p53 binding elements, is specifically immunoprecipitated by p53 in the wild type conformation (32° C., 10% of input bound). This binding is much greater in extract from cells grown at 32° C. (wt P53) than 39° C.; the small amount of binding in extract isolated at 39° C. is likely the result of a small amount of p53 protein known to exist in the wt conformation at this temperature. Likewise, a single fragment of the putative Map4 promoter region is also specifically coimmunoprecipitated by p53 antibodies in Va15 extract from cells grown at 32° C. This fragment, like the waf1 promoter fragment, is precipitated more efficiently from cells at 32° C. Other fragments of this promoter region, as well as the pBluescript vector sequences, show undetectable binding to p53. We have cloned each of these Xba I fragments of the Map4 promoter region and tested them individually for p53 binding in this assay; these studies indicate that the 850 base pair (bp) fragment that is retained by p53 in this assay maps to the region directly upstream of the candidate TATA box of the Map4 promoter region (data not shown).

The 4.3 kilobase genomic fragment containing the putative Map4 promoter has been sequenced in its entirety. There are no canonical binding sites for p53 protein in this fragment, such as those present in the mdm2 or p21/waf1 promoters. Notably, we have performed similar immunoselection studies using p53 protein purified from insect cell extract (baculovirus-p53-infected Sf9 cells). Using baculovirally-produced wt p53, we have not seen immunoselection of Map4 promoter fragments, while the p21/waf1 promoter fragment demonstrates efficient binding in this assay. The absence of consensus p53-binding sites, and the failure of wt p53 expressed in insect cells to bind to this promoter region, suggests that p53 may require another protein (co-repressor) in order to bind to the Map4 promoter.

EXAMPLE 2

Transcription Repression Complex Comprising p53, mSin3a and Histone Deacetylases In this example, the Map4 and stathmin genes were used as tools to probe the mechanism of transcriptional repression by wt p53. Recently, the work of several groups has established an evolutionarily conserved role for histone deacetylases (HDACs) in the mechanism of repression by transcription factors, such as Mad/Max, Rb, and the nuclear hormone receptors (Hassig et al., Cell 89: 341–347, 1997); (Laherty et al., Cell 89:349–356, 1997); (Nagy et al., Cell 89: 373–380, 1997); Luo et al., Cell 92: 463–473, 1998). In the experiments described below, we show that inhibition of histone deacetylase activity abrogates the ability of p53 to repress the expression of endogenous p53-target genes like Map4 and stathmin. We report the identification of p53 in complexes with the co-repressor mSin3a, along with histone deacetylase (HDAC). Only wild type p53, and not transrepression-inactive mutant forms of this protein, can be found bound to the promoter of Map4 in vivo. Additionally, mSin3a binds to the Map4 promoter only in the presence of wt p53, and when these proteins are bound, the endogenous Map4 promoter shows decreased association with acetylated histone H3. The combined data place p53 in a bona fide transcriptional repression complex, and provide the first indication that p53 may use an evolutionarily conserved mechanism for transcriptional repression: selective targeting of mSin3a, coupled to a histone deacetylase, to the regulatory regions of specific p53 repressed genes.

Materials and Methods Cell Culture:

MCF-7 cells were maintained in RPMI-1640 supplemented with 10% fetal bovine serum and 100 units/ml of penicillin and streptomycin. The A2780 ovarian carcinoma cell line, kindly provided by Tom Hamilton (Fox Chase Cancer Center), was maintained in RPMI-1640 supplemented with 10% fetal bovine serum, 100 units/ml penicillin and streptomycin, 0.3 mg/ml glutamine, and 0.25 units/ml porcine insulin. The Va15 and Vm10 murine embryo fibroblast cell lines were maintained as described (Wu, et al., Genes & Devel. 7:1126–1132, 1993);(Chen et al., Mol Med 1: 142–152, 1996). All cells were grown at 37° C. (unless otherwise noted) in a 5% $CO_2$ humidified atmosphere.

Cell Treatment/p53 Induction:

Sub-confluent cultures of MCF 7 and A2780 cells were treated with 100 nM trichostatin A (TSA, Sigma)for 2 hours, followed by incubation with 0.5 ug/ml adriamycin (doxorubicin, Sigma) for the indicated timepoints. Va15 cells grown at 39 degrees were treated with 100 nM TSA for two hours, followed by temperature shift to 32 degrees for 12 hours. p53 induction was monitored by western analysis of 100 ug protein as described (Murphy et al., Genes & Devel. 10:2971–2980, 1996), using 0.1ug/ml DO-1 (Ab-6, Calbiochem) or 421 (Ab-1, Calbiochem). MDM2 induction was monitored using the monoclonal antibody 2A10, kindly provided by Arnold Levine (Rockefeller University). For UV treatments, cells were irradiated with 4 J/m2 of UV-C with a Spectroline X series ultraviolet lamp, and output was monitored with a traceable UV light meter (Fisher Scientific). For ALLN treatment, MCF-7 cells were treated with 50 uM ALLN (calpain I inhibitor, Sigma) made in DMSO (dimethyl sulfoxide, Sigma) or with DMSO alone for 2 hours prior to harvesting.

Northern Analysis:

Total RNA was isolated from cells using CsC1 purification (Murphy et al., Genes & Devel. 10:2971–2980, 1996) or using Trizol, as per the manufacturer (Gibco/BRL). Northern analyses were performed as described (Murphy et al., Genes & Devel. 10:2971–2980, 1996). Probes for Northerns were radio labeled using random primers (Prime-It-II, Stratagene) and $\alpha^{32}P$ dCTP (NEN). Autoradiographs were quantitated using NIH image software. The average values from three independent experiments were plotted onto bar graphs following normalization to GAPDH.

Immunoprecipitation and Western Analysis:

Sub-confluent cultures of cells were harvested and lysed in NP-40 buffer supplemented with protease inhibitors (1 mM PMSF, 10 ug/ml pepstatin A, 10 ug/ml aprotinin, and 5ug/ml leupeptin). Protein concentrations were determined by the method of Bradford (BioRad). Equal ug amounts of protein (between 2.0 and 3.0 mg) were immunoprecipitated with 1 ug of each antibody, except for Va15 immunoprecipitations, which used 1000 ug protein, as described (Murphy et al., Genes & Devel. 10:2971–2980, 1996). For p300, antibody N15 (Santa Cruz Biotechnology) and AB-1 (Calbiochem) yielded similar results. Each IP was washed twice in NP-40 buffer (Wu, et al., Genes & Devel. 7:1126–1132, 1993), followed by 2 washes in RIPA buffer (50 mM Tris pH 7.4/150 mM NaCl/1% Triton X 100/0.1% SDSI 1% Na deoxycholate). Immunoprecipitations were run on 7.5–10% SDS-PAGE gels and transferred overnight onto Immuno-Blot PVDF membrane (BioRad). Western blots were blocked and incubated in antibody in PBS/0.2% Tween-20/ 5% non-fat dry milk. Blots were incubated with 1 ug/ml of antibody for 1 hour at room temperature, followed by washing in PBS/0.2% Tween-20 and incubation in peroxidase-conjugated secondary antibody (Jackson ImmunoResearch Laboratories) and chemiluminescence detection (NEN).

Chromatin Immunoprecipitations (ChIPs):

ChIPs assays were performed essentially as described (Boyd et al., Proc Natl Acad Sci 95: 13887–13892, 1998), except that lysate from 1×10$^7$ cells was diluted 8-fold in ChIP dilution buffer (0.01% SDS, 1.1% Triton X-100, 1.2 mM EDTA, 16.7 mM Tris pH 8.1, 167 mM NaCl) and bound complexes were collected with protein A agarose containing salmon sperm DNA and BSA (Upstate Biotechnology, Inc.). For ChIPs assays using antisera specific to acetylated histone H3, the Acetyl-Histone H3 ChIP assay protocol was performed exactly as specified by the manufacturer (Upstate Biotechnology, Inc.). PCR (polymerase chain reaction) of the Map4 promoter was performed on immunoprecipitated chromatin using oligonucleotides 5' AGGTGGCCGCTTCCTCGTCG 3' (forward; SEQ ID NO: 4) and 5' CTTCTCAACTTGGTCCAGC 3' (reverse; SEQ ID NO:5), as described (Boyd et al., Proc Natl Acad Sci 95: 13887–13892, 1998). PCR of the mdm2 promoter was performed using the oligonucleotides 5' GGGTCGCGCTGGCTCGT TG 3' (SEQ ID NO: 6) and 5' ATGCATTTACGAAGGAGACA 3' (SEQ ID NO: 7. In order to ensure PCR was in the linear range, 1:300 (Map4) and 1:1000 (mdm2) dilutions of DNA were amplified for a maximum of 30 cycles. For transfection experiments, asynchronously-growing H1299 cells (human lung adenocarcinoma, p53-null) were transfected using Lipofectin (Gibco/BRL) with plasmids encoding the murine Map4 promoter in pGL2-basic (10 ug) plus 2 ug of either pRc/CMV human wt p53, or pRc/CMV human p53 22/23 (courtesy of Jiayuh Lin and Arnold Levine). Thirty-six hours following transfection, lysate from cross-linked cells was immunoprecipiated with antisera to p53 (rabbit polyclonal, Santa Cruz Biotechnology) or mSin3a (AK-11, Santa Cruz Biotechnology) using the method outlined above, and PCR was performed as above. In some cases PCR products were run on 2% agarose, blotted by the method of Southern, and hybridized with the full-length Map4 promoter. Equivalent expression of the wt p53 and 22/23 mutant in transfections was monitored by western analysis of transfected cells.

In Vitro Interaction Assays:

GST-fusion proteins were prepared from E. coli cells as described (Murphy et al., Genes & Devel. 10:2971–2980, 1996). One microgram of GST or fusion protein was bound to glutathione sepharose beads and incubated with 10 uL of $^{35}$S methionine labeled, in vitro translated proteins generated in a coupled transcription/translation system (TNT, Promega). Binding occurred in 300 uL of binding buffer (20 mM Hepes pH 7.9/150 mM KC1/1 mM EDTA/4 mM MgC12/1 mM DTT/0.02% NP-40/10% glycerol) supplemented with protease inhibitors. Proteins were bound for 30 minutes at 4 degrees, and bound complexes were washed three times in wash buffer with constant vortexing (20 mM Hepes pH 7.9/150 mM KC1/1 mM EDTA/4 mM MgCl2/1 mM DTT/0.1% NP-40/10% glycerol). Bound proteins were eluted in 1× Laemmli sample buffer and separated on 7.5% or 10% SDS-PAGE. For interaction assays using only in vitro translated proteins, 15 uL of radio-labeled mSin3a was added to 15 uL of non-labeled protein in 300 uL of NP-40 buffer. After 30 minutes at 4 degrees, 0.2 ug rabbit polyclonal antisera to p53 or mSin3a (Santa Cruz Biotechnology) and 30 uL of 50% (v/v) protein A sepharose were added and incubated for 30 minutes longer at 4 degrees. Bound complexes were washed twice in NP-40 buffer, once in RIPA buffer, and resolved on SDS-PAGE.

Construction of P53 Deletion Mutants:

Deletion mutants containing the GCN4 tetramerization domain were generated by polymerase chain reaction of the plasmid PGEMhp53TZ334NR (kindly provided by Thanos Halazonetis) using forward oligos initiating at amino acid 40 or amino acid 100. In all cases, sequence analysis of the cloned PCR products revealed wild type p53 sequence.

Apoptosis Assays:

Apoptosis was quantitated using the AMC caspase assay specific for caspase 3 (Pharmingen). Vm10 cells were grown at 39 degrees or temperature-shifted to 32 degrees for 24 hours in the presence or absence of 100 nM trichostatin A (TSA). Vm10 cells at 39 degrees were treated with staurosporine (Calbiochem) at 100 nM, or dilution vehicle (dimethyl sulfoxide), or tumor necrosis factor alpha plus cycloheximide (10 ng/mL TNFα, RD Systems, plus 40 ug/mL cycloheximide, Sigma). Cells were harvested, lysed, and lysate was monitored for the caspase-3-dependent hydrolysis of the fluorogenic substrate Ac-DEVD-AMC, according to protocols derived from the manufacturer (Pharmingen). As a control for non-specific proteolysis, lysates from 39 degrees and 32 degrees were also assayed in the presence of the caspase-3 inhibitor Ac-DEVD-CHO (N-acetyl-Asp-Glu-Val Asp-aldehyde, Pharmingen). Fluorescence emissions were quantified on a spectrofluorometer (VersaFluor Cuvette Fluorometer) with excitation wavelength of 360 nm. and emission of 460 nm. The data presented represent duplicate readings of the averaged values from two (TNFα and staurosporine) or three (temperature shift) independent experiments.

Trichostatin A (TSA) Inhibits p53-mediated Repression of Endogenous Target Genes.

In order to address the possibility that transcriptional repression of Map4 and other p53-repressed genes involves a recruitment of histone deacetylases to these promoters, we tested the ability of trichostatin A (TSA) to inhibit repression of these genes following p53 induction. TSA is a potent and specific inhibitor of HDAC activity, and is active in nanomolar concentrations (Yoshida et al., J Biol Chem 265: 17174–17179, 1990). Initially for these analyses we utilized the murine cell line Va15, which harbors a temperature-sensitive p53 protein (Martinez et al., Genes & Devel., 5:151–159, 1991); (Wu, et al., Genes & Devel. 7:1126–1132, 1993). p53 exists in a mutant (inactive) conformation in this cell line at 39 degrees; temperature shift to 32 degrees results in wt p53 conformation and activity. Va15 cells were grown at 39 degrees, or temperature-shifted to 32 degrees, in the presence or absence of 100 nM TSA; similar concentrations of TSA have been shown to alleviate transcriptional repression of Mad/Max and Rb-repressed genes (Wang, et al., Mol Cell Biol 17:389–397, 1997); (Luo et al., Cell, 92:463–473, 1998). Induction of wt p53 following temperature shift of Va15 cells to 32 degrees resulted in an approximately 3-fold reduction of Map4 mRNA, consistent with our previous reports. In the presence of TSA, however, this repression was inhibited, and Map4 RNA levels maintained approximately 80% of starting levels. In contrast, neither GAPDH nor β-actin levels were altered by temperature shift, or by incubation with TSA. Flow cytometric analyses indicated that TSA treatment did not alter the cell cycle distribution of Va15 cells cultured at 32 degrees (data not shown).

To extend these observations, the human tumor derived cell lines MCF7 (breast carcinoma)and A2780 (ovarian carcinoma) were analyzed following treatment with adriamycin to activate the endogenous, wild type p53 protein. Because of difficulties detecting human Map4 message, we analyzed the mRNA levels of stathmin (also called oncoprotein 18). We recently identified stathmin as a p53-repressed gene. A time course of treatment of MCF-7 cells with the DNA-damaging agent adriamycin (doxorubicin, DOX) results in approximately 30% reduction of stathmin RNA levels after 8 hours and 75% reduction after 24 hours. We chose to focus further on the 12 hour timepoint of adriamycin treatment, where 50% repression of stathmin was evident, in order to limit the toxicity sometimes associated with TSA (Yoshida et al., J Biol Chem 265:17174–17179, 1990). Significantly, while incubation with TSA alone had undetectable effects on stathmin levels (lane 2), TSA was able to completely abrogate the reduction of stathmin levels following adriamycin treatment (lane 4). The results of three independent experiments indicate that the repression of stathmin expression evident after 12 hours of adriamycin treatment is completely abrogated by incubation with TSA. In contrast, neither the post-translational stabilization of p53 by adriamycin (DOX) nor the induction of the p53 response genes mdm2 and p21/waf1 were affected by TSA. Likewise, neither TSA nor adriamycin had any effect on stathmin levels in the H1299 human lung adenocarcinoma, which is null for p53 protein. Therefore, TSA specifically inhibits the repression of stathmin following p53 induction. We have performed identical experiments in A2780 cells (ovarian carcinoma, wt p53). In these studies, adriamycin treatment led to approximately 50% repression of stathmin expression after 12 hours; co-incubation with TSA was able to abrogate completely this repression (data not shown). The combined data indicate that HDAC activity may be an integral component of the p53-dependent repression of Map4 and stathmin.

p53 Associates with HDAC-1 and mSin3a in Vivo.

To address the possibility that p53 utilizes HDACs in order to repress transcription, we tested immunocomplexes from MCF-7 cells for the presence of a complex containing HDAC and p53.

Immunoprecipitation (IP) of MCF-7 extract with antisera specific to HDAC-1 (Santa Cruz Biotechnology) consistently revealed the presence of p53 in these immunocomplexes, as ascertained by western analysis. These complexes persisted under stringent washing conditions (RIPA buffer washes, see Materials and Methods), and were not present using control antisera (rabbit IgG, lane 1). However, in vitro binding reactions indicated that p53 was unable to bind to HDAC-1 directly. Therefore, we tested the possibility that p53 utilizes a co-repressor protein, like mSin3a, SMRT or NCoR, to couple it to HDAC. Immunoprecipitation of MCF-7 lysate using two different antibodies to mSin3a reproducibly demonstrated the presence of p53 in mSin3a complexes. In contrast, we found no evidence for an interaction between p53 and the co-repressor SMRT. Significantly, both HDAC-1 and mSin3a were present in immunocomplexes generated using p53 antisera (p53 polyclonal, lane 6, and mAb 421, data not shown). These data are a strong indication that a complex between p53, mSin3a and HDAC-1 exists in vivo. We next analyzed the p53-mSin3a interaction following post-translational stabilization of p53 mediated by DNA damaging agents. We found that the amount of p53 in mSin3a complexes was approximately five-fold greater following treatment of MCF-7 cells with doxorubicin. The significance of this increased association was unclear, however, given that p53 levels are also increased under conditions of DNA damage. To address the question of whether the avidity or affinity of p53 for mSin3a increases following DNA damage, we compared the amount of p53-mSin3a complexes following DNA damage (ultraviolet irradiation, 4J/M2) to that following treatment of cells with the calpain I inhibitor ALLN. This inhibitor has been shown to significantly stabilize p53 protein, but not activate it for DNA binding (Kubbutat et al., Mol Cell Biol 17: 460–468, 1997). Treatment of MCF-7 10 cells with 4 J/M2 Of ultraviolet radiation results in a 4–5 fold increase in p53 protein levels and a concomitant increase in p53 associated with mSin3a. Because of the stringent washing conditions we perform on these immuno-precipitations, this increased p53-mSin3a complex is not entirely reflective of the overall p53 increase. Treatment of cells with the calpain I inhibitor ALLN led to an approximately 4-fold increase in p53 protein, but an undetectable increase in the p53-mSin3a complex (lane 3). These data have been reproducible with both UV and adriamycin treatment, and support the conclusion that agents of DNA damage cause an increased affinity and/or avidity of p53 for mSin3a.

mSin3a Binds Both wt and Nutant p53 Proteins.

Several proteins that interact with wt p53 also interact with tumor-derived missense mutant alleles of this protein; these proteins include MDM2, $Taf_{II}31$ and the large T antigen of SV40 virus (Levine, Cell 88:323–331, 1997). To determine if mSin3a complexes with both mutant and wt conformations of p53 protein, we performed IP-western analyses in Val5 cells. Immunoprecipitation of Val5 cells grown at 39 degrees (mutant p53) with two different Sin3a antisera, or antisera specific to HDAC1, revealed the reproducible presence of mutant p53 in all three immuno-complexes. The presence of wt p53 in these complexes is also clearly detectable, even following washes of the immune complex in RIPA buffer. Similar results were obtained following IP with p53 antisera (421 monoclonal antibody, detects both wt and mutant conformation) followed by western analysis for mSin3a, supporting the finding that mSin3a can interact with both wt and mutant p53 protein. Consistent with this, we have found that the human tumor-derived p53 mutant R175H is able to interact with mSin3a in vitro (data not shown). These data indicate that, like other p53-binding proteins such as MDM2, $Taf_{II}31$ and SV40 large T antigen, mSin3a can interact with both mutant and wt p53. Wild type (wt) but not mutant p53 associates with mSin3a at the Map4 promoter. While it is clear from these studies that p53 associates in vivo in a complex containing mSin3a and HDAC, and that HDACs play a role in p53-mediated repression, it became important to assess the overall contribution of this complex to the repression of genes like Map4. Therefore, we performed chromatin immuno precipitations (ChIPs) of the Map4 promoter using antisera specific for p53, mSin3a and acetylated histone H3 (as per (Boyd et al., Proc Natl Acad Sci 95: 13887–13892, 1998). Initially these studies were performed in the cell line Val5, described above (Wu, et al., Genes & Devel. 7:1126–1132, 1993). Immunoprecipitation of DNA using polyclonal antisera generated against full-length p53 or mSin3a was performed on formaldehyde-cross-linked extract from cells grown at 39 degrees (mutant p53) and 32 degrees (wt p53). Following reversal of cross-links and proteinase K digestion, a fragment corresponding to nucleotides −70 to +350 of the Map4 promoter was amplified by the polymerase chain reaction (see Materials and Methods). These studies revealed that this fragment of the Map4 promoter is reproducibly present in a complex with p53 and mSin3a. Notably, this binding is detectable only when p53 is wild type, and not when this protein exists in a mutant conformation. These data indicate that, although mutant p53 can interact with mSin3a, only wild type p53 and mSin3a are present at the promoter of Map4 in vivo. Therefore, like the p53 co-activator Taf$_{II}$31 (Lu and Levine, Proc Natl Acad Sci, 92:51543–8, 1995), the mSin3a co-repressor associates with both mutant and wild type forms of p53 protein, but only the latter interaction is accompanied by DNA binding, and is therefore functionally consequential.

We extended these studies to include an analysis of the acetylation status of nucleosomes at the Map4 promoter in Va15 cells. Immunoprecipitation of Va15 cells using antisera specific for acetylated histone H3 (Upstate Biotechnology, Inc.) revealed that the Map4 promoter was preferentially associated with acetylated histone H3 when p53 was in the mutant conformation (39 degrees). Temperature shift and wild type p53 induction caused a significant decrease in the association of this promoter with acetylated histone H3 (32 degrees). The simplest interpretation of these data is that histones at the Map4 promoter are de-acetylated in the presence of wt p53. As a positive control for these studies, we analyzed by ChIPs assay the interaction of wt p53 with the mdm2 promoter. Here, only p53 in the wt conformation was able to immunoprecipitate the mdm2 promoter. Antisera to mSin3a was unable to immunoprecipitate the mdm2 promoter at either temperature. The mSin3a interaction thus appears specific to the promoter of this p53-repressed gene. Like human tumor-derived mutants of p53, the synthetic p53 double mutant at amino acids 22 and 23 (Lin et al., Genes Dev, 8:1235–46, 1994) is also unable to repress transcription of genes like Map4 (Sang et al., Oncogene 9: 853–859, 1994); (Murphy et al., Genes & Devel. 10:2971–2980, 1996). Interestingly, like mutant conformations of p53, we found that the 22/23 mutant of p53 was unable to immunoprecipitate the Map4 promoter, under conditions where wt p53 was able to bind. Following transfection of p53 into H1299 cells (p53 null), antisera to mSin3a was likewise able to immunoprecipitate the Map4 promoter only in the presence of wt p53, and not the 22/23 mutant. These data indicate that there is a consistent correlation between repression defective p53 mutants (valine135 and 22/23) and an inability to assemble with mSin3a at the Map4 promoter.

p53 and mSin3a Binding Domains.

To identify protein domains required for the p53-mSin3a interaction, we performed in vitro binding assays using GST fusion proteins of p53 and mSin3a. We first tested for the ability of a GST fusion protein of full-length p53 for the ability to associate with in vitro translated $^{35}$S-methionine-labeled mSin3a. It was found that GST p53 (amino acids 1–393) but not GST alone was able to interact with radio-labeled mSin3a following precipitation of the complex using glutathione sepharose and extensive washing. In contrast, neither GST nor GST-p53 showed an interaction with HDAC1. These results suggest that p53 recruits HDAC1 through a physical association with mSin3a, in a manner similar to that which has been reported for the Mad/Max heterodimer (Laherty et al., Cell 89:349–356, 1997). Next, we wished to determine which region(s) of p53 mediate the association with mSin3a. Similar in vitro binding assays were performed using GST fusion proteins comprised of truncated versions of p53 (corresponding to amino acids 1–160, 160–320, and 311–393). Interestingly, two distinct regions of the p53 protein, amino acids 1–160 and amino acids 311–393 were found to interact with mSin3a. Therefore, like SMRT, p53 appears to possess two discrete regions that interact with mSin3a (Nagy et al., Cell 89:373–380, 1996). It is of note that these same two mSin3a-binding domains of p53 (1–160 and 311–393) overlap with two regions previously shown to function as autonomous transrepression domains (Sang et al., Oncogene 9: 853–859, 1994); (Horikoshi et al., Mol Cell Biol 15: 227–234, 1995). To more finely map the amino-terminal region of p53 necessary for the interaction with mSin3a, we extended these studies to include mutants of p53 for which the tetramerization domain of p53 has been replaced with that of GCN4 (Waterman et al., Cancer Res, 56:158–163, 1996). These studies were necessary because our data indicate that the C-terminal mSin3a interaction domain of p53 overlaps with the tetramerization domain of p53 (amino acids 320–360; Murphy et al., unpublished data). Deletion of this domain from p53 (necessary to map the N-terminal interaction domain), however, significantly inhibited the ability of the amino terminal domain of p53 to interact with mSin3a (data not shown). Therefore, in vitro binding assays were performed using p53 synthetic mutants containing the GCN4 tetramerization domain (TZ) in place of the p53 oligomerization domain. These studies indicated that both full-length p53 containing the GCN4 tetramerization domain, and a deletion mutant in which the first 40 amino acids of p53 are deleted (A1–40;TZ) were capable of interacting with mSin3a. In contrast, deletion of amino acids 1–100 of p53 rendered the TZ mutant unable to bind (A1–100;TZ). A conservative interptretation of these data is that amino acids 40–160 of p53 are necessary for the N-terminal interaction with mSin3a.

To localize the region in mSin3a mediating the association with p53, similar in vitro interaction experiments were performed with GST p53 and truncated versions of mSin3a corresponding to amino acids 112–192 (paired amphipathic helix 1, PAM), 112–386 (PAH1–2), 297–386 (PAH 2), 297–529 (PAH2–3) and 297–965 (PAH2–4). Neither PAM nor PAH2 (lanes 6 and 9) was observed to interact with GST p53. In contrast, both PAH 2–3 and PAH 2–4 associated with GST p53 in a manner similar to that of the full-length mSin3a protein. Further delineation of the p53 binding site of mSin3a revealed that this binding domain is actually located between the second and third PAH domains of mSin3a (amino acids 392–475). The specificity of this interaction is supported by a failure of the 392–475 mutant of mSin3a to associate with the corepressor SMRT, which has been shown to require the PAH4 domain to bind mSin3a (Sang et al., Oncogene 9: 853–859,1994). These results indicate that p53 interacts with mSin3a in a region that does not include a PAH domain, but rather is located in between PAH domains 2 and 3 (amino acids 392–475).

Trichostatin A Inhibits p53-Mediated Apoptosis.

In order to assess the contribution of p53-mediated repression to apoptosis, we utilized the cell line Vm10. This murine cell line contains a stably-transfected p53 gene encoding a temperature-sensitive protein, as well as a constitutively expressed c-myc proto-oncogene; the characteristics of this line, and its ability to undergo apoptosis at 32 degrees, have been described (Chen et al., Mol Med 1:142–152, 1996). Temperature shift and wt p53 induction of these cells results in a significant increase in caspase-3 dependent AMC-DEVD hydrolysis, a read-out for apoptosis, as measured in a spectrofluorometric assay. In contrast, lysate from cells cultured at 39 degrees, or following addition of the caspase-3 inhibitor Ac-DEVD-CHO, showed negligible AMC cleavage. Culture of Vm10 cells at 32 degrees (wt p53) in the presence of 100 nM TSA resulted in a greater than 4-fold inhibition of caspase-3-dependent AMC hydrolysis. The remaining caspase-3 activity was not significantly different from Vm10 cells cultured at 39 degrees (mutant p53) and treated with TSA, indicating that this residual activity stems from toxicity associated with TSA treatment, rather than from p53 induction. We have also performed flow cytometry of Vm10 cells cultured at 39 and 32 degrees in the presence and absence of TSA, and found that 100 nM TSA reduces the sub-G1 population of Vm10 cells cultured at 32 degrees (wt p53, data not shown). TSA treatment was unable to significantly inhibit apoptosis (quantitated as caspase 3-dependent proteolysis of AMC-DEVD) induced in Vm10 cells cultured at 39 degrees (mutant p53), and treated with either staurosporine or tumor necrosis factor alpha. Therefore, the ability of TSA to inhibit apoptosis is specific for p53-dependent apoptosis.

The p53/mSin3a Complex Persists Following DNA Damage.

We next analyzed the time-course of the p53-mSin3a interaction following exposure of cells to the DNA damaging agent adriamycin (doxorubicin). Both p53-mSin3a and p53 p300 complexes were monitored by IP-western analysis in a time course following adriamycin treatment of MCF-7 cells. As a control, p53 was immunoprecipitated using polyclonal antisera generated against full-length p53 (Santa Cruz Biotechnology). p53 levels were also assessed at each time point by western analyses (data not shown). Adriamycin (DOX) treatment of MCF-7 cells resulted in a significant increase in total p53 protein after four and eight hours of treatment; this level decreased somewhat after twelve hours. Immunoprecipitation with two different antisera to mSin3a revealed a similar increase in the amount of p53 co immunoprecipitating with mSin3a antisera at 4, 8 and 12 hours post-adriamycin treatment. The p53–p300 complex was consistently more difficult to detect, and typically was present only transiently, at 4 hours post-adriamycin treatment. These results were consistent in over six independent experiments, using two different antibodies to p300, both of which immunoprecipitated similar amounts of p300 (data not shown). These data indicate that the timecourse of p53 association with mSin3a and p300 may be distinct following DNA damage; this may reflect the ability of p300 to serve as a template for the degradation of p53, mediated by MDM2 (Grossman et al., Mol Cell, 2:405–415, 1998).

Discussion

It has been clear for some time that wild type p53 can repress gene transcription (Ko, et al. Genes Dev 10:1054–1072, 1996); (Murphy and Levine, ed. CS Potten, C Booth and JW Wilson, Thompson Science, New York, 1998). Attempts to understand this activity have been complicated by the ability of p53 to repress gene transcription in a nonsequencespecific manner, particularly in reporter assays using transient transfections where p53 and target promoters are greatly overexpressed. Therefore, the relevance of transcriptional repression by p53, and elucidation of the underlying mechanism, has awaited the reliable identification of endogenous p53-repressed genes. Several groups have recently reported the existence of genes whose endogenous expression is decreased following wt p53 induction; these include the stathmin (Ahn et al., Oncogene,) and Map4 genes (Murphy et al., Genes & Devel. 10:2971–2980, 1996). Nuclear run-on analyses indicate that Map4 is repressed at the level of transcriptional initiation following p53 induction (Murphy et al., Genes & Devel. 10:2971–2980, 1996). How p53 can repress the expression of genes like Map4 has to date been unclear. Our data place p53 in a complex with a known co-repressor and HDACbinding protein, mSin3a, at the promoter of the Map4 gene. A decreased association of the Map4 promoter with acetylated histones accompanies the p53-mSin3a interaction. Mutant p53 proteins defective at transcriptional repression (valine 135 and human 22/23) are likewise defective at associating with mSin3a at the Map4 promoter. These data constitute a powerful argument that sequence-specific binding is necessary for p53mediated repression, and further that the p53-mSin3a-HDAC1 complex plays a role in transcriptional repression of gene expression mediated by p53. How p53 is targeted to the promoters of p53 repressed genes is currently an active area of study by several groups. We have cloned and characterized the Map4 promoter, and shown that a specific fragment of this promoter interacts with wt p53, but not mutant forms of this protein, in a sequence-specific manner (Hoffman and Murphy, manuscript in preparation). Notably, however, this promoter lacks a canonical p53-response element, so this binding activity apparently involves a novel DNA binding site. Additionally, while p53 imrnunopurified from mammalian nuclear extract is capable of interacting with the Map4 promoter, p53 protein purified from baculovirus-p53 infected insect cells is not (Hoffman and Murphy, manuscript in preparation). It is possible that at least one other protein, not present in insect cells, is required to target p53 to the promoter of Map4, and perhaps to other repressed promoters as well. Recently, two groups have identified DNA binding elements involved in p53-mediated transcriptional repression. One group found that a p53 "half-site" (two palindromic pentamers of consensus 5' PuPuPuCA/TT/AGPyPyPy3' (SEQ ID NO: 12)) allows p53 to repress the HBV enhancer (Ori et al., 1998, EMBO J. 17:544–553). Similarly, Lee and colleagues found that a perfect half site, possibly coupled with an imperfect pentamer, competes with HNF-3 and represses the alpha-feto-protein gene (Lee et al., 1999 Mol Cell Biol 19:1279–1288). As the Map4 promoter contains neither a perfect nor an imperfect pentamer site, it is likely that an entirely novel binding element for repression exists for this promoter. However, the mechanism of repression (coupling of mSin3a and HDAC) may well be conserved for all three of these promoters.

Our in vitro data indicate that there is most likely a direct interaction between p53 and mSin3a. However, as these studies used in vitro translated proteins, we cannot exclude the formal possibility that a protein present in reticulocyte lysate mediates this interaction. We have mapped the domain necessary for the p53-mSin3a interaction to two regions of p53 protein, from amino acids 40–160 and 320–360 (human p53). Notably, these two domains of p53 overlap with those previously implicated in transcriptional repression by p53 (Sang et al., Oncogene 9: 853–859,1994); (Horikoshi et al., Mol Cell Biol 15: 227–234, 1995). We have also shown that nanomolar concentrations of TSA can effectively inhibit p53-dependent apoptosis, but does not detectably affect p53-dependent transactivation, nor apoptosis induced by staurosporine or TNFα. These data argue for a role for p53-dependent transrepression in apoptosis induction by this protein, and are consistent with reports, that MDM2 protein, which inhibits transrepression by p53 (Chen et al., Mol Med, 1:142–152, 1995), also inhibits p53-dependent apoptosis in the Vm10 cell line (Chen et al., Mol Med 1: 142–152, 1996). These data are further supported by a recent report from Koumenis et al. (manuscript submitted). In this study, these investigators found that during p53 induction mediated by hypoxia, p53 functions as a transcriptional repressor of genes like Map4 and stathmin, but does not detectably activate the expression of genes like bax and p21/waf1. Further, uncoupling of the mSin3a-HDAC1 complex markedly inhibits apoptosis induced by p53 in hypoxic cells (Koumenis et al., manuscript submitted). The p53-HDAC interaction may have further functional significance. Recently it was demonstrated that p53 interacts with the co-activator p300, as well as the closely-related protein CBP (Avantaggiati et al., Cell 89:1175–1184, 1997); (Lill et al., Nature, 387:823–827, 1997). Both of these proteins have histone acetyl transferase (HAT) activity, and also interact with another HAT protein, pCAF-1 (Blanco et al., Genes Dev 12:1638–1651, 1998). The p53–p300 interaction has been shown to be critical for both transactivation (Avantaggiatti et al, Cell, 89:1175–1184, 1997; Lill et al., Nature, 387:823–827, 1997) and apoptosis induction (Avantaggiatti et al, Cell, 89:1175–1194, 1997) by p53. Additionally, however, p53 was shown to be a substrate for acetylation by this protein (Gu and Roeder, Cell 90:595–606, 1997). Acetylation of p53 on lysine 382 has been demonstrated to relieve part of the negative regulation of p53 conferred by the C-terminus of this protein (Gu and Roeder, Cell, 90:595–606, 1997); Sakaguchi et al., Genes Dev 12:2831–2841, 1998), and may represent an important post-translational modification of p53 following DNA damage (Giaccia and Kastan, Genes Dev 12: 2973–2981, 1998). Our data indicate that, in addition to associating with histone acetyl-transferases, p53 also associates with HDACs. These data raise the formal possibility that, in addition to contributing to transrepression of genes like stathmin and Map4, the HDAC mSin3a-p53 association may also result in the de-acetylation of p53, and play a role in the regulation of this protein. The data presented herein support the hypothesis that mSin3a plays a role in p53-mediate transcriptional repression by tethering p53 in a repressor complex with HDACs.

EXAMPLE 3

Transcriptional Repression of Survivin Gene Expression by Wild Type p53

The survivin gene encodes an apoptosis inhibitor that was first identified as a gene with a coding region complementary to the effector cell protease receptor, EPR-1. Although these genes share homology in their coding regions, they are transcribed in a reverse direction, and appear to share no regulatory or promoter regions (Ambrosini et al., 1997, Nat Med 3:917–921). Sequence of the survivin coding region revealed a conserved motif present at the amino terminus that identified this protein as a member of the IAP (inhibitor of apoptosis) family. This motif, or BIR domain, (baculovirus IAP repeat) has been shown to mediate the interaction with, and inhibition of, the caspase family of proteolytic enzymes (Tamm et al., 1998, Cancer Res 58:5315–5320; Devereaux and Reed, 1999, Genes & Dev 13:239–252). Caspases catalyze the penultimate destruction of cells by the process of apoptosis, or programmed cell death; this process is now acknowledged to be a critical mechanism whereby cells exhibiting uncontrolled proliferation, which is the hallmark of transformation, are eliminated. Consequently, elevated expression of survivin would be predicted to promote tumorigenesis, and in fact survivin is highly expressed in many tumor types.

Survivin expression is normally developmentally regulated; it is expressed widely in fetal tissues, but becomes restricted during development, and appears to be negligibly expressed in the majority of adult tissues (Ambrosini et al., 1997, supra; Adida et al., 1998, Am J Pathol 152:43–49). Sometime during tumorigenesis this gene appears to be re-activated. That this re-activation is important for tumorigenesis is supported by the finding that expression of anti-sense RNA for survivin is sufficient to induce apoptosis in human tumor cell lines (Ambrosini et al., 1998, supra; Li et al., 1998, Nature 396:580–584; Olie et al., 2000, Cancer Res 60:2805–2809). Additionally, elevated survivin levels have been shown to be a marker of poor prognosis for several tumor types, including neuroblastoma, colorectal and gastric carcinoma (Adida et al., 1998, Am J Pathol 152:43–49).

The expression of survivin is also cell-cycle regulated. This gene shows little expression in the G1 phase of the cell cycle, but is highly expressed in G2/M phase (Li et al., 1998, supra). For the human survivin promoter, this cell cycle regulation has been shown to rely on the presence of two proximal CDE sites (cell cycle dependent elements) downstream of the transcriptional start site (Li and Altieri, 1999. Biochem J 344:305–311.). During mitosis, survivin protein binds the mitotic spindle, and there is evidence that via this interaction survivin monitors mitotic spindle integrity, eliminating by apoptosis those cells with aberrantly-formed mitotic spindles (Li et al., 1998, 1999, supra). This role for survivin is evolutionarily-conserved, as it is shared among survivin homologues in yeast (Uren et al., 1999, Proc Natl Acad Sci 96:10170–10175) and *C. elegans* (Fraser et al., 1999, Curr Biol 9:292–301). Although de-regulation of survivin gene expression appears to be a common and significant event in tumorigenesis, little is known regarding how this gene's expression becomes re-activated in tumor cells.

Like survivin, p53 is also a critical mediator of apoptosis and tumorigenesis. Unlike survivin, p53 promotes apoptosis and thereby actively inhibits the process of cellular transformation. p53 is a nuclear transcription factor that is latent in normal cells, but becomes activated by a variety of cellular stresses, such as DNA damage, hypoxia (insufficient oxygen) and aberrant cellular proliferation. Following activation of p53, this protein functions as a sequence-specific binding protein and transcription factor. p53 up-regulates genes that promote cell death, such as bax, fas, KILLER/DR5 and IGF-BP3 (for review see Levine, Cell 88:323–331, 1997). p53 also negatively regulates some proteins that can inhibit the progression of apoptosis, such as presenilin-1 and Map4 (Murphy et al., Genes & Devel. 10:2971–2980, 1996). Although little is known about the binding site for p53 in repressed promoters, the mechanism of repression by p53 has been shown to require sequence-specific DNA binding, and to involve interaction with histone deacetylases, mediated by the co-repressor protein mSin3 (Murphy et al., 1999, supra).

In several studies, the transcriptional repression activity of p53 has been implicated in p53-dependent apoptosis (Walker and Levine, Proc Natl Acad Aci 93:15335–15340, 1996); (Ryan and Vousden, Mol Cell Biol, 18:3692, 1998); (Sakamura et al., Oncogene 15:887–898, 1997); Venot et al., EMBO J, 17:4668–4679, 1998), raising the possibility that p53 may repress genes with anti-apoptotic activity. In a search for genes that are negatively regulated by p53, we and others identified several genes with roles in mitotic spindle formation and integrity, as well as the control of G2/M, that are repressed following induction of wild type p53. These genes include stathmin, Map4 and β-tubulin (Ahn et al., Oncogene); (Murphy et al., Genes & Devel. 10:2971–2980, 1996); (Zhao et al., 2000). See Examples 1–2. These studies prompted us to test the possibility that survivin, which binds to the mitotic spindle and exhibits anti-apoptotic activity, might likewise be subject to negative regulation by p53. As described herein, we have identified survivin as a gene that is potently repressed, at both the RNA and protein levels, following p53 induction in a variety of cell lines. Immunobinding analyses and chromatin immunoprecipitations indicate that p53 binds to a region of the survivin promoter in a sequence-specific manner. Interestingly, the negative regulation of survivin by p53 is mediated by a novel p53 binding site, coupled with a CDE/CHR element located immediately downstream of this element. Deletion of either the p53-binding site, or the CDE/CHR element, effectively abolishes the ability of p53 to repress this promoter. The p53 binding site located in the survivin promoter is similar to the p53 binding site present in the promoters of trans-activated genes (El-Deiry et al., Natl Genet 1:45–49, 1992); (Tokino et. al., 1994, Human Mol Gen 3:1537–1542.), but a spacer region between the palindromic pentamers appears to be critical in the function of this sequence as a repressing element.

The following materials and methods are provided to facilitate practice of Example 3.

Materials and Methods

Cell Culture, p53 Induction.

MCF-7 cells were maintained in RPMI-1640 supplemented with 10% fetal bovine serum and 100 units/ml of penicillin and streptomycin. The human melanoma cell line CaCl, and the derivative clone expressing the HPV E6 gene, were cultured as described (Ahn et al., Oncogene). The human osteosarcoma cell lines Saos-2 and U2-OS (kindly provided by Peter Adams, Fox Chase Cancer Center), the murine p21 knock-out fibroblasts (kindly provided by James Sherley, MIT) and the human lung adenocarcinoma cell line H1299 were cultured in DMEM supplemented with 10% fetal bovine serum and 100 units/ml of penicillin and streptomycin. Murine Va15 cells, containing the temperature-sensitive Valine 135 allele of p53, were maintained as described (Wu, et al., Genes & Devel. 7:1126–1132, 1993). All cells were grown at 37° C. (unless otherwise noted) in a 5% $CO_2$ humidified atmosphere. For treatment with ultraviolet light, cells were irradiated with 0–10 J/m2 (as noted) of UV-C with a Spectroline X series ultraviolet lamp, and output was monitored with a traceable UV light meter (Fisher Scientific). For drug treatment, cells were treated with 0.5ug/ml adriamycin (doxorubicin, Sigma), or dilution vehicle alone, for twenty-four hours. p53 induction was monitored by western analysis of 100 ug protein as described (Murphy et al., Genes & Devel. 10:2971–2980, 1996), using 0.1ug/ml DO-1 (Ab-6, Calbiochem) or 421 (Ab-1, Calbiochem.

Reverse Transcription-Polymerase Chain Reaction (RT-PCR), Northerns.

The full-length coding region for survivin was generated by reverse transcription-polymerase chain reaction (RT-PCR) using 5 ug of total RNA from the H1299 human lung adenocarcinoma cell line, using the Access RT-PCR kit (Promega) and the following oligonucleotides: forward 5' ATGAGATACCATGGGTGCCCCGACG 3' (SEQ ID NO: 8), reverse 5' TTAAGGATCCCTGCTCGATGGCACG 3' (SEQ ID NO: 9). The cDNA was cloned into the Topo TA vector (Invitrogen) and subjected to DNA sequence analysis for sequence confirmation. Total RNA was isolated from cells using CsCl purification (Murphy et al., Genes & Devel. 10:2971–2980, 1996) or using Trizol, as per the manufacturer (Gibco/BRL). Northern analyses were performed as described (Murphy et al., Genes & Devel. 10:2971–2980, 1996). Probes for Northerns were radio labeled using random primers (Prime-It-II, Stratagene) and $^{32}P$ dCTP (NEN). Autoradiographs were quantitated using NIH image software.

PCR of the Survivin Promoter, Deletion Constructs.

Approximately 1.1 kb of the survivin promoter region was generated by polymerase chain reaction and cloned into the Topo TA vector, using the following oligonucleotides: forward 5' CTGGCCATAGAACCAGAGAAGTGA 3' (SEQ ID NO: 10), reverse 5' CCACCTCTGCCAACG GGTCCCGCG 3' (SEQ ID NO: 11), to generate the plasmid SpI. This sequence represents nucleotides 1821–2912 of the human survivin gene, accession number U75285. DNA sequence analysis confirmed the sequence of this region. The survivin promoter was then cloned into the promoterless luciferase vector pGL2-basic (Promega) to generate the plasmid SpII, for use in transfections and luciferase assays. For deletion of the p53 binding site in the survivin promoter, the SpII plasmid was digested with SacII to eliminate the p53 binding site and re-ligated, to generate SpII Sac. The SpV deletion construct was generated from the SpII plasmid following digestion with SmaI and HindIII, generation of blunt ends by Klenow fill-in, ligation; this promoter construct contains nucleotides 2331–2912 of the human survivin gene linked to the firefly luciferase gene.

Transfections, Luciferase Assays.

H1299 cells were seeded in 6-well plates at $2\times10^5$ cells/well, and allowed to settle overnight. The next morning cells were transfected with 1.5 ug of firefly luciferase reporter construct, 1.5 ug Renilla luciferase construct (pRL-CMV or pRL-tk, Promega) and 0–25 ng of p53 expression plasmid (in pRc/CMV) using Fugene, according to protocols derived from the manufacturer (Roche). After 48 hours, the cells were harvested, lysed and dual luciferase assays were performed as per the protocol derived from the manufacturer (Promega) on a Monolight 2010 luminometer (Analytical Luminescence Laboratory). Luciferase activity was normalized to total protein levels, as well as to Renilla luciferase activity.

Kinase Assays, Flow Cytometry.

Cyclin-dependent kinase assays were performed essentially as described (Harper et al., 1993), using 250 ug of whole cell extract immunoprecipitated with 0.5 ug of polyclonal antisera to cdk2 (Santa Cruz Biotechnology), cyclin E and cyclin A. Following immunoprecipitation and washing, 1 ug of histone H1 (Sigma) was used as a substrate, in kinase reaction buffer (20 mM Tris pH 7.4/7.5 mM MgCl2/1 mM DTT), supplemented with 5 mM sodium fluoride, 1 mM sodium ortho-vanadate, and 125 ng/uL cAMP-dependent protein kinase inhibitor (Sigma). 0.5 uL of $^{32}P$-ATP (NEN, 800 Ci/mmol) was added to each reaction, and 0.5 ug of normal rabbit IgG (Sigma) was used as a negative control. Following incubation at 37 degrees for 20 minutes, reactions were boiled in Laemmli sample buffer and loaded onto 10% SDS-PAGE. Cells for flow cytometry were fixed in ethanol and stained with propidium iodide as described (Murphy et al., Genes & Devel. 10:2971–2980, 1996) and analyzed on a Becton Dickinson FacScan. G1, S (synthesis) and G2/M populations were calculated using the program CellQuest.

Modified McKay Assays (Immunobinding).

Immunoselection of the p53-binding site in the survivin promoter was performed essentially as described (Wu, et al., Genes & Devel. 7:1126–1132, 1993). Briefly, 250 ug of whole cell extract from 10.1 (p53 null) or Va15 cells grown at 32 degrees (wt p53) was incubated with 300,000 cpm of end-labeled probe for the survivin promoter in McKay binding buffer (10% glycerol/5 mM EDTA/20 mM Tris pH 7.2/100 mM NaCl/0.1% NP-40) supplemented with 1.25 ug/uL poly dI/dC (Pharmacia) and 1 ug each 421 and 1620 mAb. Following incubation for 1 hour at 4° C., immune-complexes were collected with protein A sepharose and washed extensively in McKay washing buffer (2% glycerol/5 mM EDTA/20 mM Tris pH 7.2/100 mM NaCl/0.1% NP-40), resuspended in 10 mM Tris pH 7.4/1 mM EDTA pH 8, phenol-chlorform extracted, precipitated, and resolved on 4% non-denaturing acrylamide gels. For competition experiments, a fifty-fold molar excess of unlabled DNA was pre-incubated for 10 minutes prior to the binding reaction.

SDS-PAGE and Western Analysis.

Western analysis was performed essentially as described (Murphy et al., 1999). Briefly, subconfluent cells were harvested and lysed in RIPA buffer (50 mM Tris at pH 7.4, 150 mM NaCl, 1% Triton X-100, 0.1% SDS, and 1% sodium deoxycholate) supplemented with protease inhibitors (1 mM PMSF, 10 mg/ml pepstatin, 10 mg/ml aprotinin, and 5 mg/ml leupeptin). Protein concentrations were determined using the Bio-Rad $D_c$ Protein Assay (Bio-Rad). Equal amounts of protein (between 50 and 120 ugs) were run on 10% or 12% SDS-polyacrylamide gels and transferred overnight onto PVDF membrane (Bio-Rad). Western blots were incubated in antibody in 5% nonfat dry milk in phosphate-buffered saline supplemented with 0.2% Tween 20 (PBST). Blots were incubated with primary antibody at the following dilutions: p53 Ab-6 (Calbiochem) 1:1000, actin, AC-15 (Sigma) at 1:5000, p21/waf1 (Calbiochem) 1:1000 and survivin (Novus) 1:1000. Blots were washed with PBST and incubated in horseradish peroxidase-linked secondary antibody (Jackson ImmunoResearch Laboratories) and developed via the chemiluminescence protocol provided by the manufacturer (NEN).

Cell Lines and Cell Culture

The following human cancer cell lines (and their tissue of origin) were used for further studies: A2780, OVCAR3, OVCAR5, OVCAR8, OVCAR10, SKOV3, PEO1, and UPN251 (ovary); HT29 (colon); MCF7 (breast); H1299 (lung); and HeLa (uterus). ROSE-TAg is a tumorigenic cell line derived from Fisher 344 rat ovarian surface epithelial (ROSE) cells transformed with simian virus 40 (SV40) large T antigen (TAg) in vitro. NuTu19 and NuTu26 are spontaneously transformed cell lines derived from Fisher 344 ROSE cells (Testa et al. Cancer Research (1994) 54:2778–84). IG10 and IF5 are spontaneously transformed mouse ovarian surface epithelial (MOSE) cell lines (Roby et al. Carcinogenesis (2000) 21: 585–91). Mc6 is a mammary cancer cell line derived from a mammary tumor of a mammary tumor-prone C3(1)/TAg transgenic mouse line and Pr14 is a prostate cancer cell line derived from a prostate tumor of a prostate cancer-prone line of C3(1)/TAg transgenic mice (Jorcyk et al. Prostate (1998) 34:10–22). Normal MOSE cells were isolated from the ovaries of C57BL/6 adult mice and used for up to three passages. Normal ROSE cells were isolated from the ovaries of Fisher 344 rats and used for up to five passages. Normal human ovarian surface epithelial (HOSE) cells were derived from normal human ovaries. NIH 3T3 is an immortalized, nontumorigenic mouse fibroblast cell line. All cell lines were maintained at 37° C. in a humidified incubator with an atmosphere of 5% $CO_2$/95% air. HOSE, A2780, OVCAR3, OVCAR5, OVCAR8, OVCAR10, SKOV3, PEO1, UPN251, ROSE-TAg, NuTu19, NuTu26, MCF7, and normal ROSE cells were cultured in RPMI 1640 medium (GibcoBRL, Gaithersburg, Md.) supplemented with 10% fetal bovine serum (FBS). IG10, IF5, Mc6, Pr14, and MOSE cells were cultured in Dulbecco's modified Eagle medium (DMEM; Gibco-BRL) plus 5% FBS. NIH 3T3 cells were cultured in DMEM plus 10% calf serum, and H1299 and HeLa cells were cultured in DMEM plus 10% FBS. All media were supplemented with streptomycin (100 μg/mL), penicillin (100 units/mL), glutamine (0.3 mg/mL), and pork insulin (0.25 unit/mL or 1× ITS [insulin, transferrin, and selenium], Gibco BRL, Rockville, Md.).

Vector Construction

A 1092-base-pair fragment of the human survivin gene (nucleotides 1821–2912, GenBank accession number U75285) was excised from plasmid SpI with restriction enzymes KpnI and XhoI (Hoffman et al. JBC (2001) submitted).

The secreted alkaline phosphatase (SEAP) expression vector under control of the survivin promoter (pSRVN-SEAP) was constructed by subcloning the KpnI-XhoI fragment into the multiple cloning site of the SEAP expression vector pSEAP-Basic (Clontech, Palo Alto, Calif.). To generate stable transfectants, the pSRVN-SEAP-NEO plasmid was constructed by subcloning the SRVN-SEAP sequence (a KpnI-XbaI fragment) from pSRVN-SEAP into the PC3 vector, a modified pcDNA3 vector (Invitrogen, San Diego Calif.,) without the cytomegalovirus promoter.

Transient Transfection

The pSRVN-SEAP plasmid was transiently transfected into cell lines by use of the TransIT-LT1 transfection reagent (PanVera, Madison, Wis.). Briefly, $3 \times 10^5$ cells were placed into each well of a six-well plate in 2 ml of complete medium. After an overnight incubation, cells were 40%–50% confluent, and a mixture of 2 μg of pSRVN-SEAP plasmid, 0.2 μg of pGL3-Control plasmid, 6 μL of LT1 transfection reagent, and 100 μL of serum-free medium was added to each well. The pGL3-control plasmid (Promega), which is a luciferase expression vector driven by the SV40 promoter, was used to assess transfection efficiency and hence normalize each transfection. Two other plasmids, pSEAP-Basic (a promoterless SEAP construct) and pSV40-SEAP (a SEAP expression vector with the SV40 promoter) (Clontech), were also used for each cell line as negative and positive controls, respectively. Medium (100 μL) was removed 48 hours after transfection and used to determine SEAP activity, after normalization of the transfection efficiency. Briefly, the adherent cells were washed once with PBS, exposed to 1 mL of lysis buffer (Promega), and scraped from dishes with a cell scraper. After centrifugation of the cell lysates at 15.7 rcf for 1 minute, the supernatants were removed and stored at −70° C. until luciferase activity was assayed. Luciferase activity was determined by mixing 5 uL of supernatant with 100 μL of luciferase assay reagent (Promega) and determining the relative luminescence with a luminometer (Analytical Luminescence System). This procedure allowed us to adjust the amount of conditioned medium used to allow for differences in transfection efficiency.

Stable Transfection

The pSRVN-SEAP-NEO plasmid was linearized with restriction enzyme PvuI and purified by phenol-chloroform extraction and ethanol precipitation. Before electroporation, subconfluent A2780 cells were trypsinized, washed twice with PBS, and resuspended at $10 \times 10^6$ cells in 0.7 mL of PBS. The cell suspension was transferred into a Gene Pulser cuvette (Bio-Rad Laboratories, Hercules, Calif.) and 5 μg of linearized pSRVN-SEAP-NEO or control vector PC3 was added. After 10 minutes on ice, the cells were subjected to electroporation by using the Gene Pulser II System (Bio-Rad Laboratories) at a voltage of 250 V/cm and a capacitance of 975 µF and then plated in three 10-mm Petri dishes with complete medium. One day later, medium was changed to complete growth medium supplemented with G418 at 500 µg/mL. After 2 weeks, the G418-resistant clones were isolated with cloning cylinders. SEAP activity in the conditioned medium from individual clones was determined when the cells were nearly confluent.

Animal Study

Female CB17/ICR SCID (severe combined immunodeficient) mice, approximately 8 weeks of age and weighting approximately 20 g, were used to establish orthotopic ovarian tumors. All these mice were bred in the Laboratory Animal Facility at Fox Chase Cancer Center, maintained in specific pathogen-free conditions, and received commercial food and water ad libitum. Institution guidelines were followed in handling the animals. To establish the orthotopic tumors, cultured A2780 transfectants (two SRVN-SEAP-NEO clones, A2780$^{SSN1}$ and A2780$^{SSN2}$, and one vector control clone, A2780$^{PC3}$) were harvested with 0.05% trypsin-EDTA (GibcolBRL), washed in PBS, and resuspended in RPMI 1640 complete medium at 40×10$^6$ cells per mL. Before intrabursal implantation of tumor cells, eight SCID mice were anesthetized with a 15:3:5:152 mixture of ketamine-HCl (100 mg/mL), acepromazine malleate (10 mg/mL), xylazine hydrochloride (20 mg/mL) (Ford Dodge Animal Health, Ford Dodge, IA), and 0.9% normal saline, injected intraperitoneally at 10 µL/g of body weight. The skin was disinfected with Wescodyne and 70% ethanol. A small incision was made on one side of the back to locate the ovary. The oviduct was held with small forceps, and a 26-gauge needle connected to a syringe was inserted into the oviduct and was passed through the infundibulum until the needle tip reached the space between bursa and the ovary. Approximately 20 µL of the cell suspension (about 0.8×10$^6$ cells) was injected into the intrabursal space. The needle was slowly removed, the ovary was replaced in the abdominal cavity, and the body wall was closed with sutures. One ovary of each animal was injected.

Plasma for SEAP analysis was obtained by orbital puncture with heparinized glass tubes (Fisher Scientific, Pittsburgh, PA) on days 0, 1, 3, 6, and 9 after cell implantation. About 20 µL of plasma was obtained after the blood was centrifuged at 4.5 rcf for 7 minutes (Bao et al. (2000) Gynecol Oncol 78:373–9). Animals were sacrificed 14 days after implantation; ovaries were removed, embedded in paraffin, and sectioned for histopathologic analysis.

SEAP Assay

SEAP activity in culture medium or plasma was determined by a chemiluminescence or fluorescence method using Great Escape SEAP kits from Clontech (Bronstein et al. Biotechniques (1994) 17:172–4). Briefly, 5-µL samples were mixed with 45 uL of dilution buffer and incubated in a oven at 70° C. for 45 minutes. Sixty microliters of assay buffer containing L-homoarginine was then added. After a 5-minute incubation at room temperature, the samples were exposed to 60 µL of chemiluminescent substrate CSPD (disodium 3-(4-methoxyspiro (1.2 dioxetane-3,2'-(5'-chloro) tricyclo (3.3.1.1)-decan) 4-yl) phenyl phosphate) (1.25 mM) or 3 µL of fluorescent substrate 4-methylumbelliferyl phosphate (Clontech). Chemiluminescence was measured with a luminometer (Analytical Luminescence System) after a 10-minute incubation at room temperature. After a 60-minute incubation in the dark, fluorescence was measured with a CytoFluor II fluorometer (Bio-Rad Laboratories) with excitation and emission wavelengths of 360 nm and 449 nm, respectively. SEAP activity was determined from a standard curve.

To determine whether exogenous SEAP could be separated from endogenous placental alkaline phosphatase of pregnant animals, plasma from two C57BL/6 pregnant mice at embryonic day 12, one normal control mouse and one CB17/ICR SCID mouse carrying an A2780$^{SEAP13}$ cell implant was isolated. Five µl plasma was mixed with 45 µl dilution buffer and treated with 70° C. heat for 0, 20, 40, or 60 minutes. The alkaline phosphatase activity was determined, as described.

Results

Figure 3A:
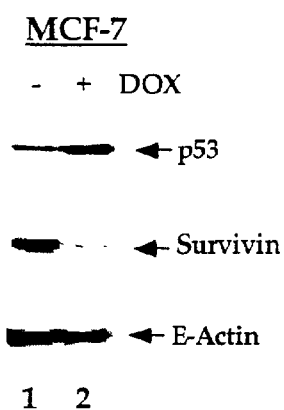
FIGS. 3A–3C.
Figure 3B:
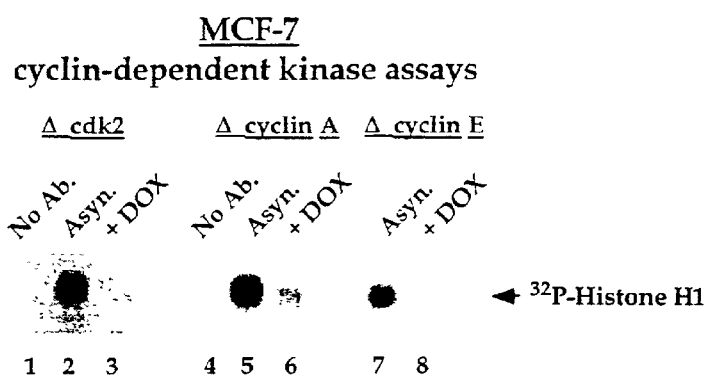
Figure 3C:
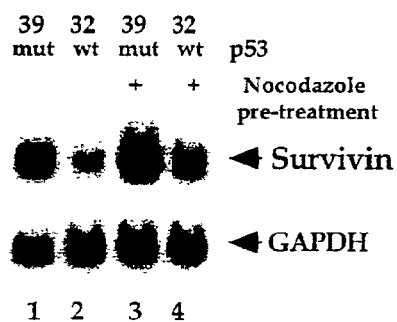

FIG. 3 shows p53 induction in human MCF7 breast carcinoma cells leads to down-regulation of survivin protein. Western analysis of p53 induction in human MCF7 breast carcinoma cells, following twenty-four hour treatment with doxorubicin, was performed to induce DNA damage and activate p53. While this treatment results n a 4-fold induction of p53 expression, protein levels of survivin are decreased 3–4 fold. A β-actin control is shown to verify equal protein loading in the lanes.

FIG. 3B shows cyclin-dependent kinase assays which indicate that MCF7 cells treated with doxorubicin arrest in G2/M phase, where survivin expression is normally high. Immunoprecipitation of catalytically active cdk2 (lanes 2–3), cyclin A (lanes 5–6) and cyclin E (lanes 7–8) indicate that, while these kinase activities are high in asynchronously growing MCF7 cells (lanes 2, 5, and 7), all activities are low in cells treated with doxorubicin (lanes 3, 6 and 8). This finding is consistent with flow cytometry data, which indicate that these cells are arrested in G2/M (not shown). As a negative control, normal rabbit IgG is used instead of polyclonal antisera for the immunoprecipitations and kinase assays (lanes 1 and 4).

FIG. 3 C shows that cells arrested in G2/M with nocodazole maintain the ability to down-regulate survivin following induction of p53 by temperature shift. Va15 cells (temperature-sensitive p53 which is wild type at 32 degrees) were grown at 39 degrees (mutant p53, asynchronous growth), and arrested in G2/M following twenty-four hours of nocodazole treatment. These cells were then subjected to twelve hours of temperature shift to induce wild type p53. While treatment with nocodazole alone resulted in increased survivin expression, as expected (lane 3), p53 induction in cells G2/M-arrested with nocodazole still resulted in decreased survivin expression (lane 4). The combined data indicate that p53 induction can repress survivin gene expression independent of p53's ability to induce G1 arrest in cells.

FIG. 4 shows the results from a series of experiments which indicate that survivin is down-regulated at the RNA level following p53 induction. Induction of wt p53 in human breast carcinoma cells (MCF7) and melanoma cells (CaCl) following doxorubicin (DOX) treatment results in marked decreases in mRNA levels for survivin, as early as twelve hours following treatment (0.5 ug/mL doxorubicin). In contrast, DOX treatment result in increased expression of the p53-induced gene p21/waf1, while the RNA levels of gapdh remain unchanged. See FIG. 4A.

Figure 4A:
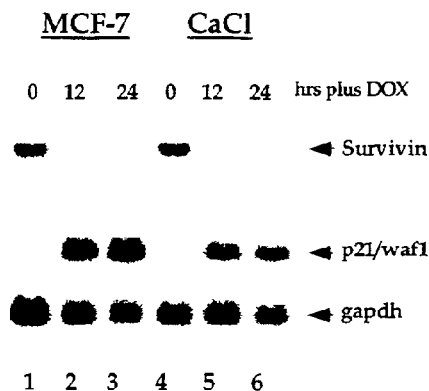
Figure 4B:
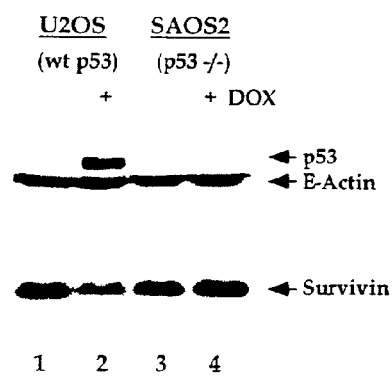
Figure 4C:
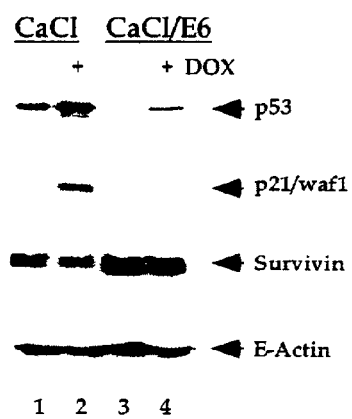

As shown in FIG. 4B, survivin down-regulation requires the presence of wt p53. Western analysis of the human osteosarcoma cell lines Saos2 (p53-null) and U20S (wt p53) following doxorubicin treatment results in decreased survivin protein levels only in cells with wt p53 (U20S). A β-actin control is included to verify equal protein loading in the lanes.

The human papillomavirus E6 protein, which targets p53 for degradation, is sufficient to inhibit doxorubicin-mediated down-regulation of survivin. Western analysis of the human melanoma cell line CaCl, and a derivative cell line expressing the HPV E6 protein (CaCl/E6) reveals that treatment with doxorubicin results in down-regulation of survivin protein levels only in parental CaCl cells, which contain functional p53. As a positive control for p53 induction, immunoblots of the p53-induced gene p21/waf1 are included. A β-actin control is included to verify equal protein loading in the lanes. See FIG. 4C.

Figure 4D:
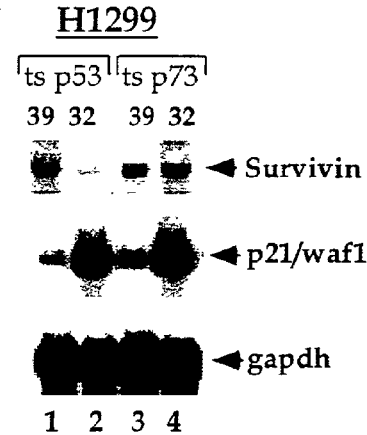

FIG. 4D shows that inducible p53, but not p73, negatively regulates survivin gene expression. Northern analysis of survivin levels in H1299 cells (p53-null human lung adenocarcinoma) containing stably-transfected alleles for temperature-sensitive p53 (Valine 138, lanes 1–2) or p73 (lanes 3–4). Cells were grown at 39 degrees (mutant conformation, lanes 1 and 3) or following temperature shift to 32 degrees for 24 hours (wild type p53/p73 induction). While both proteins are capable of inducing the trans-activated gene p21/waf1 at 32 degrees (lanes 2 and 4), only p53 was capable of down-regulating survivin expression (lane 2). A gapdh control is included to verify equal loading and integrity of RNA.

FIG. 4E shows the results of flow cytometry of H1299 ts-p53 and ts-p73 cells which indicate that both cell types arrest at G1 and G2/M at 32 degrees. The percent of cells evident in the G1, S, and G2/M phases of the cell cycle in cells grown at 39 degrees (mutant/inactive protein, asynchronous growth) and following 24 hour temperature shift to 32 degrees (wt protein induced) are shown. The data presented are the average from two independent experiments.

FIG. 5 shows that ultra-violet irradiation leads to survivin down-regulation in a p53-dependent manner, but not in a p21/waf1-dependent manner. Dose-dependent decreases in survivin gene expression in MCF7 breast carcinoma cells (FIG. 5A) and U20S osteosarcoma cells (FIG. 5B) following ultra-violet irradiation. Cells were treated with the indicated dose of radiation, harvested twenty-four hours later, and subjected to western analysis for p53 and survivin. A β-actin control is included to verify equal protein loading in the lanes. Identical irradiation of p53-null SaoS2 cells (FIG. 5C) results in minor decreases in survivin levels.

Figure 5A:
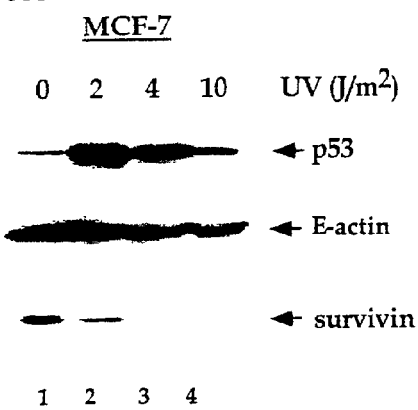
FIGS. 5A–5D. A series of western blots showing that ultra violet irradiation leads to survivin down regulation in a p53-dependent manner, but not in a p21/waf1-dependent manner. Dose-dependent decreases in survivin gene expression in MCF7 breast carcinoma cells (FIG. 5A) and U20S osteosarcoma cells (FIG. 5B). Identical irradiation of p53- null SaoS2 cells results in only minor decreases in survivin levels (FIG. 5C). Western analysis of murine embryo fibroblasts from the p21/waf1 knock-out mouse reveal dose-dependent decreases in survivin levels in these cells, indicating that p21/waf1 is not necessary for repression of survivin following p53 induction (FIG. 5D).
Figure 5B:
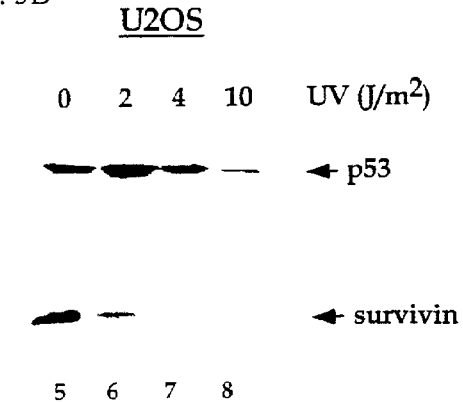
Figure 5C:
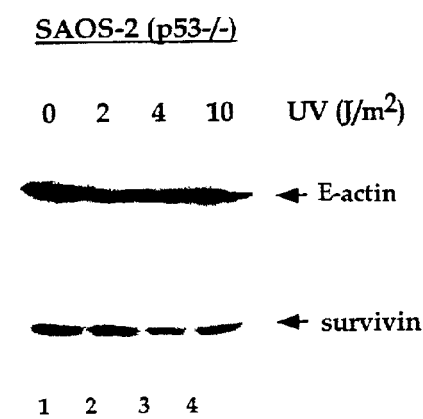
Figure 5D:
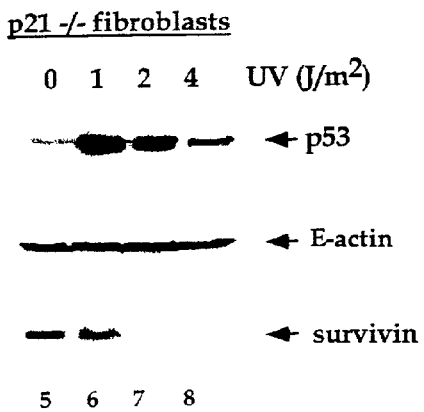

FIG. 5D shows the results of western analysis of murine embryo fibroblasts from the p21/waf1 knock-out mouse which reveal dose-dependent decreases in survivin levels in these cells, indicating that p21/waf1 is not necessary for repression of survivin following p53 induction.

FIG. 6 shows that the survivin promoter is sufficient to confer negative regulation of the firefly luciferase gene by p53. The survivin promoter, ligated to the promoterless firefly luciferase gene, was stably-transfected into cells containing temperature-sensitive p53 (Val5 cells). Temperature shift to 32 degrees induces wt p53 protein, and down-regulation of luciferase mRNA, as depicted in this Northern analysis. Expression of gapdh is shown as a control for RNA loading and integrity. See FIG. 6A.

FIG. 6B shows that the full length survivin promoter linked to the firefly luciferase gene (this construct is denoted SpII, and is described in the Materials and Methods section) is repressed by p53 in transfected cells, when luciferase levels are normalized to the co-transfected Renilla luciferase control.

FIG. 7 shows that p53 binds in a sequence-specific manner to a fragment of the survivin promoter. The radio-labeled survivin promoter, but not the vector control, is specifically retained by p53 antisera in cells with wt p53 (Val5 32 degrees, lane 2), but not in cells that are null for p53 (10.1 cells, p53 –/–, lane 2). 20% of the radiolabeled vector/insert is loaded in the input lane. See FIG. 7A.

Immunobinding assay using the radio-labeled promoter constructs listed, incubated with whole cell extract from cells with wt p53, as well as monoclonal antisera specific for p53. Following binding reactions, bound DNA is immunoprecipitated, washed, and resolved on a non-denaturing acrylamide gel. The radio-labeled vector fragment serves as an internal negative control, and two fragments from the mdm2 promoter serve as a positive control. The SpV construct encodes 500 bp of the survivin promoter; the SpV-p53BS encodes the same fragment, with the p53 binding site deleted. As a control for sequence-specific binding, a 50-fold molar excess of each construct was pre-incubated with the extract for 10 minutes prior to the binding reaction (+ competition). (Competition between this unlabeled DNA and the radio-labeled DNA is indicative of sequence-specific binding, which unlike non-specific DNA binding has a binding equilibrium). 10% of the radiolabeled vector/insert is loaded in the input lane. See FIG. 7B.

FIG. 7C shows the nucleotide sequence of the p53-repressible element in the survivin promoter. The three consensus p53 binding sites are underlined, and the spacer elements are in bold. The CDE and CHR, which are also necessary for p53-mediated repression by this element, are in italics. The minimal p53 repressing element encompasses nucleotides 2723–2775 (SEQ ID NO: 3) of the survivin gene promoter (GenBank Accession No: U75285. This element alone can confer p53 mediated repression of gene expression.

FIG. 8A shows the result of Northern analysis of cells with temperature-sensitive p53 (p53 is wild type and active at 32 degrees) that have been stably-transfected with the firefly luciferase gene driven by the p53-repressing element depicted in FIG. 7C (wt SPVI), or a construct in which the three underlined 10 base pair p53 binding sites have been deleted (Δ p53 BS), or in which the p53 binding site is intact, but the CDE/CHR has been deleted. FIG. 8B shown below this figure is quantitation of the level of luciferase mRNA in these cells, normalized to the level of the housekeeping gene glyceraldehyde 6-phosphate dehydrogenase. FIG. 8C shows the results of luciferase assays in transiently-transfected cells, that have been supplemented with 0, 10 or 25 nanograms of p53 plasmid. While the p53-repressing element depicted in FIG. 7C is capable of conferring repression by p53, deletion of the 3 nucleotide spacer element (spacer 1) converts this site to a trans-activating element.

The nature of the p53 binding site in the promoters of p53-repressed genes has not been clearly elucidated until now. This study identifies survivin as a p53-repressed gene; this repression is shown to be distinct from induction of G1 arrest by p53. While p53 is capable of repressing the survivin promoter, the p53-homologue p73 is not. Immunobinding assays indicate that p53 binds the survivin promoter at a site distinct from a canonical p53 response element, which consists of two pairs of palindromic pentamers separated by 0–1 base pairs. Instead the survivin site resembles those first identified for p53 by immunoselection protocols, containing a larger spacer between the pairs of palindromic pentamers. Significantly, deletion of this three-nucleotide spacer is sufficient to convert the survivin binding site from a repressing element into a trans-activating element. The combined data also indicate that the CDE/CHR element, which is present in a number of cell cycle regulated genes but which has not previously been associated with repression by p53, is required, along with the p53 binding sites, in order to create a fully functional p53-repressing element. This element, along with the Map4 promoter element, constitute the first nucleotide sequences that are sufficient to confer repression by p53 in a stably-transfected, as well as a transiently transfected, cell. These elements should prove invaluable in the creation of biological elements that seek to destroy cancer cells based on their absence of functional p53 protein.

Additional studies were performed to assess the activity of the survivin promoter in a variety of different tumor types. We constructed the pSRVN-SEAP plasmid to determine whether the survivin promoter functioned in cancer cells. Promoter activity was determined from the SEAP activity in conditioned medium from transiently transfected cells. In A2780 cells transfected with the promoterless pSEAP-Basic plasmid, SEAP expression was almost baseline (Table 1). In several other cancer cell lines, SEAP expression was also almost baseline, but in others the promoterless plasmid had some activity. In all cancer cell lines transfected with a plasmid containing the survivin promoter (i.e., pSRVN-SEAP), SEAP expression was five-fold to about 400-fold higher than that observed with the promoterless pSEAP-Basic plasmid (Table 1). However, early-passage normal ROSE and MOSE cells similarly transfected showed less SEAP expression when transfected with pSRVN-SEAP than with pSEAP-Basic (Table 1). To determine the relative promoter activity of the survivin promoter compared with the relatively strong SV40 viral promoter, we transfected the various cell lines with the SV40 promoter-driven SEAP expression plasmid pSV40-SEAP and measured SEAP expression. The survivin promoter was more active in the cancer cell lines, and the SV40 promoter was more active in the nontransformed cell lines (i.e., NIH 3T3, ROSE, and MOSE cells) (Table 1).

To determine whether the survivin promoter could induce enough SEAP activity to monitor tumor growth in vivo, we created stable A2780 transfectants harboring stably integrated SRVN-SEAP-NEO. Two clones (A2780$^{SSN1}$ and A2780$^{SSN2}$) were selected because of their relatively high SEAP production. These two SRVN-SEAP-NEO clones and one vector control clone (A2780PC3) were used to generate orthotopic ovarian tumors by injection into the intrabursal space of mouse ovaries to mimic early ovarian cancer. After tumor cell implantation, plasma was collected at designated intervals to measure SEAP activity. SEAP activity was detected as early as 24 hours in animals implanted with $0.8 \times 10^6$ cells from either of the two SRVN-SEAP-NEO clones and increased with time and tumor growth. In contrast, SEAP activity was not detected in the animal injected with the vector control clone. Paraffin sections prepared from ovaries removed on day 14 had small tumors in the intrabursal cavity in all mice injected with a pSRVN-SEAP-NEO clone (A2780$^{SSN}$) or the vector control clone (A2780$^{PC3}$) Contralateral ovaries were normal.

To determine whether endogenous alkaline phosphatase activity could be separated from transgenic SEAP activity, we used heat to inactivate the endogenous activity. Plasma from normal control mice, pregnant mice, and a mouse carrying A2780$^{SEAP13}$ cells was treated with heat for 0, 20, 40, or 60 minutes, and alkaline phosphatase activity was determined. Alkaline phosphatase activity in plasma of normal and pregnant mice decreased quickly after the heat treatment at 70° C. and was still low 40 minutes later. However, plasma alkaline phosphatase activity in the mouse xenografted with A2780$^{SEAP13}$ cells had not decrease after 60 minutes of heat treatment. Therefore, exogenous SEAP activity can be monitored during tumor development and effectively separated from endogenous alkaline phosphatase activity by heat treatment.

TABLE I

Activity of survivin promoter relative to a promoterless or simian virus 40 (SV40) promoter-driven secreted alkaline phosphatase (SEAP) plasmid in cell lines with various origins*

| Cell type | pSEAP-Basic (1) | pSRVN-SEAP (2) | pSV40-SEAP (3) | Ratio (2)/(1) | Ratio (2)/(3) |
|---|---|---|---|---|---|
| A2780 | 100 ± 20 | 16,000 ± 900 | 5,400 ± 400 | 70 | 3 |
| OVCAR3[s] | 5,000 ± 600 | 67,000 ± 12,000 | 40,000 ± 1,100 | 13 | 2 |
| SKOV3 | 80 ± 30 | 41,000 ± 1,800 | 20,000 ± 1,300 | 460 | 2 |
| NuTu19 | 20 ± 1 | 5,500 ± 400 | 3,100 ± 200 | 360 | 2 |
| IF5 | 200 ± 20 | 3,000 ± 900 | 1,400 ± 100 | 16 | 2 |
| IG10 | 200 ± 10 | 1,200 ± 30 | 600 ± 20 | 5 | 2 |
| Mc6 | 300 ± 40 | 11,000 ± 800 | 4,300 ± 300 | 42 | 3 |
| Pr14 | 50 ± 0 | 1,000 ± 10 | 600 ± 30 | 21 | 2 |
| MCF7[s] | 1,500 ± 200 | 160,000 ± 4,500 | 84,000 ± 5,600 | 110 | 2 |
| HeLa[s] | 43,000 ± 3,700 | 8,800,000 ± 17,000 | 4,000,000 ± 230,000 | 204 | 2 |
| HT29[s] | 21,000 ± 400 | 8,800,000 ± 6,300 | 4,600,000 ± 48,100 | 409 | 2 |
| H1299[s] | 95,000 ± 1,200 | 8,400,000 ± 250,000 | 4,200,000 ± 110,000 | 90 | 2 |
| NIH 3T3 | 80 ± 20 | 600 ± 50 | 1,100 ± 200 | 7 | <1 |
| ROSE[s] | 15,000 ± 3,700 | 8,100 ± 2,700 | 26,000 ± 2,300 | 1 | <1 |
| MOSE[s] | 14,000 ± 2,000 | 110,000 ± 18,000 | 430,000 ± 47,000 | 8 | <1 |

*SEAP analyses (indicated with a superscripted s) were done by the luminescence method and expressed as relative luminescence units. Other analyses were done by the fluorescence method and expressed as relative fluorescence units. ROSE = rat ovarian surface epithelial; MOSE = mouse ovarian surface epithelial.

Survivin transcripts were the fourth most frequently overexpressed transcript in common human cancers (e.g., melanoma and cancers of the colon, brain, breast, and lung) relative to levels in normal cells as determined by SAGE analysis (Velcuescu et al. Nat. Genet. (1999) 23:387–8), indicating that survivin provides a target for the development of beneficial agents for the treatment of cancer. If increased survivin activity is controlled transcriptionally, then the survivin promoter might control transgene expression in a cancer-specific manner. Indeed transcriptional regulation of survivin expression in cancer cells has been reported (Li et al. Biochem J. (1999) 344:305). Using approximately 1 kilobase of the 5' upstream regulatory region of the survivin gene to drive SEAP expression in ovarian, mammary, colon, lung, and uterine cervical cancer cell lines, we have shown that the survivin promoter can control gene expression regardless of tumor type, mechanism of oncogenesis, and species, and we have confirmed that survivin expression appears to be transcriptionally activated, at least in part.

In contrast to adult tissues, where survivin expression is largely limited to activation during oncogenesis, in the human fetus, survivin is abundantly expressed in apoptosis-regulated tissues. Similarly, survivin was nearly ubiquitously expressed in embryonic mouse tissues at an early gestational stage (embryonic day 11.5) but was later expressed more selectively. Increased survivin expression and survivin promoter activity in cancer cell lines indicate that transcriptional factors needed for survivin transcription reappear or are reactivated during oncogenesis. The approximately 1-kilobase fragment of the survivin promoter used in this study contains the CHR (cell cycle gene homology region) and abundant SP1, CDES, E2F transcription factor binding sites that are believed to be responsible for control the transcription of survivin.

As indicated above, our interest in the survivin promoter first arose because of a desire to drive transgene expression in a cancer-specific manner for cancer gene therapy, to improve gene delivery progress, to specifically regulate expression of transgenes to limit the toxicity of therapeutic genes such as herpes simplex virus thymidine kinase, and to create a tumor-selective replicative oncolytic virus. We believe that the survivin promoter's specificity and expression in many early-stage cancers make it an excellent candidate for these purposes. Lastly, this cancer specific reporter system has major implications for monitoring tumor initiation and progression in tumor prone transgenic animals.

The following sequences are provided to facilitate the practice of the invention:

```
             Length: 3523  Aug. 19, 1999 08:57 Type: N Check: 5463
   1 AGAGAAACCC TGTTTCGAAA AAACAAAACA CAAAACAAAA CTCAAAACAA           SEQ ID NO: 1

51 AAAAGACACA GTCTCATTAT ATGGCTCAGG CTGTTCTTGA CCTTAGGTGG

101 CCTAGTTGAC CTTAACTTGG TATCCAATTG CCTCAGCACA CAATGCCAGG

151 GCATCCTTTT GCTCTCTTAG GTTTTTTTTT TTTAATTAAT TAAAAAAAAT

201 TTTAAAAGAT TTATTTATTA TATCTAACTA CACTGTAGAT GTCTTCAGAT

251 GCACCAAAGA GGATGTCAGA TCTCATTATA GATGGTTGTG AGCCACCATG

301 TGGTTGCTGG GATTTGAACT CAGGACCTCT AGGAGAGCAA GCAGTCAGTG

351 CTCTTACCCG CTACGCCATC TCCCCAGCCC TAAAATTTTT TTGAGATAGG

401 CTCTCACCAT CTCTCTGGCT TGCATGGAAT AAGCTGTGTA AATCAGGCTG

451 AACTTGAGCT CACAGAGATC TGCCTGCCTC TGCCTCTCAA GTGCTGGGAT

501 TAAAGGTGTG TATTGTTACA TTAGGTTAGT TACTATGATT TTTTAAAATA

551 TGATTTAATA TATATGAGCA CATTGTAGCT GTCTTCAGAC ACACGACACA

601 CCAGAAGAGG GCATCAATTT CCATGACAGA TGGTTTTGAG CCACCATGTT

651 GTGGCTGGGA ATTGAACTCA GGACCTCTAG Aaaccagtca gtgctcttaa 701 ccgctgaccc atttctccag ttactatggc tttaacagta aactatgtct 751 actaaatcgt aagtaactat gtatgtactt taggacagtt actaatatgg 801 atctcatgta tattatcatc atctccattt actgcttaaa tgaatgagta 851 ttgtgtgaca aaactttccc tggggaaatg caatacagaa gtctacttat 901 cccagagagg aaactcatga caaaccaaag cccagcttgg tgaaccaatt 951 agtttttattg gggctacctt cagtactatg atgaaatatg agtgaggggg 1001 tactgacagt agcaqaaatg actcaaagac agctgaatca ccaaggccca 1051 ccccaatact ggtaacaact cacaaattgg gaaaactggg gcacactgca 1101 tagcctgcag gccactcaat gggttgagta agtaaggctg gtctaaacct 1151 cttccaggcg gcttggctgg tctctgcttc tctcaggcag ctggtctggt 1201 cttaagagtc tgcaactttt gctcttctga gaatcttctt tactgcgtag 1251 gtcttctttt ctgagaggac gctgaactct ggcaggaaag tagcctagta 1301 aaactagatg gtttcagggg ccttcctgct taatggaaag ttccaatctt 1351 ggaggaaact gttacacaaa gaaaggttta gaagtcttcc acaggttaac
```

-continued

```
1401 ataatttgtt tagccatgct gagacttcat cgggaatatg gtatttacct
1451 tttggcatcc tattagtaac tttattgaga gtgactatta tctaattttc
1501 ataaacgagg aaactgaggc ttacctttcc taaggctaca aaagcacagc
1551 tgtacttcct aaccaagttc tcctggtaac ccctatatgc ctgagtttac
1601 aatcctagca cctggctact gaagttaaag ccccactagc caaacattgt
1651 cttgttgaca ctgtggtgtt actaaacttg cctgttaaca taatgagaat
1701 gaggagtgct ggagagaaaa ttaaactatt aaagataagg ctcataacta
1751 aaactacaaa gggcactgag gatatattaa ccatgtaggc ctcttgtgat
1801 gattaagata tgtggatcat ggaataagca taaaggagtt gggtatcact
1851 atttcttctg gaccagtact atgcacaggc aatataatgt gaccgtagtg
1901 acactctaga ggagggggc ggggagagga gagtaggagg aggtaatttt
1951 agctgtgtat ggcggctcaa atttgtaatc tcaacactca ggaggctgag
2001 gctgagggat tgccatcact ctgagggagg tgggtgatgc aaagtgaatt
2051 tcaggccagc ctgcgctatg gtgggaggca ctgtgcaaaa aacccaaaac
2101 agaacaaagg tgatctttaa gttttcaagt aactacgttg aaaaaagaaa
2151 aaaactaaaa gaaacatgaa attatttaag ttactaaaata cactcccatt
2201 atataatcag tttttcttgt ttgtttgttt gtttttcgag acagggtttc
2251 tctgtagagc cctggctgtc ctggaccttta ctttgtagac caggctggcc
2301 tcgaactcag aaatccgcct gcctctgcct cccgagtgct gggttaaagg
2351 tgcgccacca cgcccggccc catataatca gttttgcatt caacaatgaa
2401 ccttctcaac ttggtccagc caggtttcag gcagctacta tgacggcgcc
2451 ctcagctccc agtagttctg cgttagcagt gtaacccaag cccgcccgc
2501 cctcccagta catcatagtg cccaccagtc aggCCgggcc ggcggggccc
2551 actcaggccc acccgtacgc aggcgcgtgc gcctgacact agcatccttt
2601 ctgctggaaa aggaagcggc ggccctctca gaacggcgga ggcggcctga
2651 gcctcgccat tcgctgaggc atccgcgggc gggaggcgag TCTAGAcccc
2701 cgacgcgcgc cgcgccaacg gtccgccact cgtgctgctt ccacggagag
2751 ggcgaggagt aggggccggc gtggattggt tcgcggcgcc tcggcccgcc
2801 cttCGGTGGc gcccattggc tggggcggca cccgctgacg gcgagcacgc
2851 tccgccttcg tgccggcctt caagagggcg acgaggaagc ggccacctcc
2901 ctgtgccccg cccctccggc taggtctgtg gcttctgcgg ctcctcccgg
2951 ctgctcccgg ctcctctctg ccctctcccg gcttcctgcg gctccggctt
3001 gggctcggcg gcggcggcgg gtaggtgcgg ctgtgattga gatcggaggg
3051 tcggcctcct cactaacctc cacgactccc gcccaggttc tcgcggtggc
3101 cgccggggac cccgcaggtc cctcccgagg cggggaaggg cggtggctgt
3151 ccgcctacgg gacgccgggg tggttgagag agggggcctg gtgggggcc
3201 tgcgggcgtg accttcggag tttctgagac gccttctgag gggaccgtag
3251 gggcgaggc gggcggagag attttgtatc agggcttcgg aggttgtgga
3301 gccgagggc ttgcctcagg ctgggcatgt gctgagccgg gacactgagg
3351 gtcgactgca gcctgggccc ttgggtgggg ttcgggatgc agaaggacgc
```

```
3401 cggggtcgtt tctccaggct tcaggagggg cgtccgtgta tgtggggact 3451 gaggcgagct ctgcgtgtcc cttctggggg ttatgggtgg ggccgagggg 3501 tggtctggag aatccaactc gag
```

SEQ ID NO: 2

```
1820             CTGGCCATAG AACCAGAGAA GTGAGTGGAT
GTGATGCCCA GCTCCAGAAG TGACTCCAGA ACACCCTGTT CCAAAGCAGA
GGACACACTG ATTTTTTTTT TAATAGGCTG CAGGACTTAC TGTTGGTGGG
ACGCCCTGCT TTGCGAAGGG AAAGGAGGAG TTTGCCCTGA GCACAGGCCC
CCACCCTCCA CTGGGCTTTC CCCAGCTCCC TTGTCTTCTT ATCACGGTAG
TGGCCCAGTC CCTGGCCCCT GACTCCAGAA GGTGGCCCTC CTGGAAACCC
AGGTCGTGCA GTCAACGATG TACTCGCCGG GACAGCGATG TCTGCTGCAC
TCCATCCCTC CCCTGTTCAT TTGTCCTTCA TGCCCGTCTG GAGTAGATGC
TTTTTGCAGA GGTGGCACCC TGTAAAGCTC TCCTGTCTGA CTTTTTTTTT
TTTTTTAGAC TGAGTTTTGC TCTTGTTGCC TAGGCTGGAG TGCAATGGCA
CAATCTCAGC TCACTGCACC CTCTGCCTCC CGGGTTCAAG CGATTCTCCT
GCCTCAGCCT CCCGAGTAGT TGGGATTACA GGCATGCACC ACCACGCCCA
GCTAATTTTT GTATTTTTAG TAGAGACAAG GTTTCACCGT GATGGCCAGG
CTGGTCTTGA ACTCCAGGAC TCAAGTGATG CTCCTGCCTA GGCCTCTCAA
AGTGTTGGGA TTACAGGCGT GAGCCACTGC ACCCGGCCTG CACGCGTTCT
TTGAAAGCAG TCGAGGGGGC GCTAGGTGTG GGCAGGGACG AGCTGGCGCG
GCGTCGCTGG GTGCACCGCG ACCACGGGCA GAGCCACGCG GCGGGAGGAC
TACAACTCCC GGCACACCCC GCGCCGCCCC GCCTCTACTC CCAGAAGGCC
GCGGGGGGTG GACCGCCTAA GAGGGCGTGC GCTCCCGACA TGCC
CCGCGGCGCGCCATTA ACCGCCAGAT TTGAATCGCG GGACCCGTTG
GCAGAGGTGGCGGCGGCGGC ATGGGTGCCC CGACGTTGCC CCCTGCCTGG
CAGCCCTTTCTCAAGGACCA CCGCATCTCT ACATTCAAGA ACTGGCCCTT
CTTGGAGGGCTGCGCCTGCA CCCCGGAGCG    2920
```

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. An isolated nucleic acid molecule comprising a Map4 promoter region, wherein said promoter region is contained in SEQ ID NO.1.

2. An expression vector comprising the nucleic acid molecule of claim 1.

3. The vector of claim 2, wherein said vector is an expression vector operably linked to a heterologous gene encoding a gene product.

4. The vector of claim 3, wherein said heterologous gene is a reporter gene.

5. The vector of claim 3, wherein said heterologous gene is selected from the group consisting of luciferase, secreted alkaline phosphatase, GFP and chloramphenicol acetyltransferase.

6. An isolated host cell transformed with the vector of claim 3.

7. The host cell of claim 6, wherein said host cell is a prokaryotic cell.

8. The host cell of claim 6, wherein said host. cell is a eukaryotic cell.

9. The host cell of claim 8 which is a human cell.

10. The host cell of claim 8 which is a tumor cell.

11. An isolated nucleic acid molecule comprising a survivin promoter region, wherein said promoter region is contained in SEQ ID NO.2.

12. An expression vector comprising the nucleic acid molecule of claim 11.

13. The vector of claim 12, wherein said vector is an expression vector operably linked to a heterologous gene encoding a gene product.

14. The vector of claim 13, wherein said heterologous gene is a reporter gene.

15. The vector of claim 14, wherein said heterologous gene is selected from the group consisting of luciferase, secreted alkaline phosphatase, GFP and chloramphenicol acetyltransferase.

16. An isolated host cell transformed with the vector of claim 12.

17. The host cell of claim 16, wherein said host cell is a prokaryotic cell.

18. The host cell of claim 16, wherein said host cell is a eukaryotic cell.

19. The host cell of claim 18 which is a human cell.

20. The host cell of claim 19 which is a tumor cell.

21. A minimal p53 repressible element having the sequence of SEQ ID NO: 3.

22. A DNA construct comprising the element of claim 21.

23. An isolated nucleic acid molecule comprising the minimal p53 repressible element of claim 21.

24. A vector comprising the nucleic acid molecule of claim 23.

25. The vector of claim 24, wherein said vector is an expression vector and said minimal p53 repressible element is operably linked to a heterologous gene encoding a gene product.

26. The expression vector of claim 25, wherein said heterologous gene is a reporter gene.

27. The expression vector of claim 26, wherein said heterologous gene is selected from the group consisting of luciferase, secreted alkaline phosphatase, green fluorescent protein, and chloramphenicol acetyltransferase.

28. An isolated host cell transformed with the expression vector of claim 25.

29. The host cell of claim 28, wherein said host cell is a prokaryotic cell.

30. The host cell of claim 28, wherein said host cell is a eukaryotic cell.

31. The host cell of claim 30 which is a human cell.

32. The host cell of claim 30 which is a tumor cell.

33. A process for producing a host cell containing a heterologous gene operably linked to the minimal p53 repressible element of claim 21 which comprises:
   a) transfecting a cell with an expression vector comprising said heterologous gene operably linked to the minimal p53 repressible element of claim 21, said expression vector operably comprising a selectable marker gene; and
   b) selecting transformed host cells on the basis of said transformed cells containing a heterologous gene operably linked to the minimal p53 repressible element of claim 21.

34. The expression vector of claim 25, wherein said heterologous gene is the herpes simplex virus thymidine kinase gene.

35. The vector of claim 24, wherein said minimal p53 repressible element is operably linked to a sequence encodingfor an antisense molecule.

36. The vector of claim 35, wherein said antisense molecule is specific for a nucleic acid encoding for a protein selected from the group consisting of bcl-2, survivin, and P-glycoprotein.

* * * * *

SEQUENCE LISTING

```
<160> NUMBER OF SEQ ID NOS: 13

<210> SEQ ID NO 1
<211> LENGTH: 3523
<212> TYPE: DNA
<213> ORGANISM: murine

<400> SEQUENCE: 1
agagaaaccc tgtttcgaaa aaacaaaaca caaaacaaaa ctcaaaacaa aaaagacaca     60
gtctcattat atggctcagg ctgttcttga ccttaggtgg cctagttgac cttaacttgg    120
tatccaattg cctcagcaca caatgccagg gcatcctttt gctctcttag gtttttttttt   180
```

```
tttaattaat taaaaaaaat tttaaaagat ttatttatta tatctaacta cactgtagat      240
gtcttcagat gcaccaaaga ggatgtcaga tctcattata gatggttgtg agccaccatg      300
tggttgctgg gatttgaact caggacctct aggagagcaa gcagtcagtg ctcttacccg      360
ctacgccatc tccccagccc taaaatttt ttgagatagg ctctcaccat ctctctggct       420
tgcatggaat aagctgtgta atcaggctga aacttgagct cacagagatc tgcctgcctc      480
tgcctctcaa gtgctgggat taaaggtgtg tattgttaca ttaggttagt tactatgatt      540
ttttaaaata tgatttaata tatatgagca cattgtagct gtcttcagac acacgacaca      600
ccagaagagg gcatcaattt ccatgacaga tggttttgag ccaccatgtt gtggctggga      660
attgaactca ggacctctag aaaccagtca gtgctcttaa ccgctgaccc atttctccag      720
ttactatggc tttaacagta aactatgtct actaaatcgt aagtaactat gtatgtactt      780
taggacagtt actaatatgg atctcatgta tattatcatc atctccattt actgcttaaa      840
tgaatgagta ttgtgtgaca aaactttccc tggggaaatg caatacagaa gtctacttat      900
cccagagagg aaactcatga caaaccaaag cccagcttgg tgaaccaatt agttttattg      960
gggctacctt cagtactatg atgaaatatg agtgagggg tactgacagt agcagaaatg      1020
actcaaagac agctgaatca ccaaggccca ccccaatact ggtaacaact cacaaattgg     1080
gaaaactggg gcacactgca tagcctgcag gccactcaat gggttgagta agtaaggctg     1140
gtctaaacct cttccaggcg gcttggctgg tctctgcttc tctcaggcag ctggtctggt     1200
cttaagagtc tgcaactttt gctcttctga gaatcttctt tactgcgtag gtcttctttt     1260
ctgagaggac gctgaactct ggcaggaaag tagcctagta aaactagatg gtttcagggg     1320
ccttcctgct taatgaaaag ttccaatctt ggaggaaact gttacacaaa gaaaggttta    1380
gaagtcttcc acaggttaac ataatttgtt tagccatgct gagacttcat cgggaatatg    1440
gtatttacct tttggcatcc tattagtaac tttattgaga gtgactatta tctaatttc     1500 ataaacgagg aaactgaggc ttaccttttcc taaggctaca aaagcacagc tgtacttcct    1560
aaccaagttc tcctggtaac ccctatatgc ctgagtttac aatcctagca cctggctact    1620
gaagttaaag ccccactagc caaacattgt cttgttgaca ctgtggtgtt actaaacttg    1680
cctgttaaca taatgagaat gaggagtgct ggagagaaaa ttaaactatt aaagataagg    1740
ctcataacta aaactacaaa gggcactgag gatatattaa ccatgtaggg ctcttgtgat    1800
gattaagata tgtggatcat ggaataagca taaaggagtt gggtatcact atttcttctg    1860
gaccagtact atgcacaggc aatataatgt gaccgtagtg acactctaga ggaggggggc    1920
ggggagagga gagtaggagg aggtaatttt agctgtgtat ggcggctcaa atttgtaatc    1980
tcaacactca ggaggctgag gctgagggat tgccatcact ctgagggagg tgggtgatgc    2040
aaagtgaatt tcaggccagc ctgcgctatg gtgggaggca ctgtgcaaaa aacccaaaac    2100
agaacaaagg tgatctttaa gttttcaagt aactacgttg aaaaaagaaa aaactaaaa     2160 gaaacatgaa attatttaag ttactaaata cactcccatt atataatcag ttttttcttgt   2220 ttgtttgttt gtttttcgag acagggtttc tctgtagagc cctggctgtc ctggaccttta   2280 ctttgtagac caggctggcc tcgaactcag aaatccgcct gcctctgcct cccgagtgct    2340
gggttaaagg tgcgccacca cgcccggccc catataatca gttttgcatt caacaatgaa   2400
ccttctcaac ttggtccagc caggtttcag gcagctacta tgacggcgcc ctcagctccc   2460
agtagttctg cgttagcagt gtaacccaag cccgccccgc cctcccagta catcatagtg   2520
cccaccagtc aggccgggcc ggcggggccc actcaggccc accgtacgc aggcgcgtgc    2580
```

```
gcctgacact agcatccttt ctgctggaaa aggaagcggc ggccctctca gaacggcgga      2640
ggcggcctga gcctcgccat tcgctgaggc atccgcgggc gggaggcgag tctagacccc      2700
cgacgcgcgc cgcgccaacg gtccgccact cgtgctgctt ccacgagagg ggcgaggagt      2760
aggggccggc gtggattggt tcgcggcgcc tcggcccgcc cttcggtggc gcccattggc      2820
tggggcggca cccgctgacg gcgagcacgc tccgccttcg tgccggcctt caagagggcg      2880
acgaggaagc ggccacctcc ctgtgccccg cccctccggc taggtctgtg gcttctgcgg      2940
ctcctcccgg ctgctcccgg ctcctctctg ccctctcccg gcttcctgcg gctccggctt      3000
gggctcggcg gcggcggcgg gtaggtgcgg ctgtgattga gatcggaggg tcggcctcct      3060
cactaacctc cacgactccc gcccaggttc tcgcggtggc cgccggggac ccgcaggtc       3120 cctcccgagg cggggaaggg cggtggctgt ccgcctacgg gacgccgggg tggttgagag      3180 aggggggcctg gtgggggggcc tgcggcgcgtg accttcggag tttctgagac gccttctgag   3240
gggaccgtag ggggcgaggc gggcggagag attttgtatc agggcttcgg aggttgtgga      3300
gccgaggggc ttgcctcagg ctgggcatgt gctgagccgg gacactgagg gtcgactgca      3360
gcctgggccc ttgggtgggg ttcgggatgc agaaggacgc cggggtcgtt tctccaggct      3420
tcaggagggg cgtccgtgta tgtgggggact gaggcgagct ctgcgtgtcc cttctgggggg   3480 ttatgggtgg ggccgagggg tggtctggag aatccaactc gag                       3523

<210> SEQ ID NO 2
<211> LENGTH: 1100
<212> TYPE: DNA
<213> ORGANISM: murine

<400> SEQUENCE: 2
ctggccatag aaccagagaa gtgagtggat gtgatgccca gctccagaag tgactccaga        60
acaccctgtt ccaaagcaga ggacacactg attttttttt taataggctg caggacttac       120
tgttggtggg acgccctgct ttgcgaaggg aaaggaggag tttgccctga gcacaggccc       180
ccaccctcca ctgggctttc cccagctccc ttgtcttctt atcacggtag tggcccagtc       240
cctggcccct gactccagaa ggtggccctc ctggaaaccc aggtcgtgca gtcaacgatg       300
tactcgccgg gacagcgatg tctgctgcac tccatccctc ccctgttcat ttgtccttca       360
tgcccgtctg gagtagatgc ttttttgcaga ggtggcaccc tgtaaagctc tcctgtctga     420
cttttttttt tttttttagac tgagttttgc tcttgttgcc taggctggag tgcaatggca       480
caatctcagc tcactgcacc ctctgcctcc cgggttcaag cgattctcct gcctcagcct       540
cccgagtagt tgggattaca ggcatgcacc accacgccca gctaattttt gtattttttag       600 tagagacaag gtttcaccgt gatggccagg ctggtcttga actccaggac tcaagtgatg       660
ctcctgccta ggcctctcaa agtgttggga ttacaggcgt gagccactgc acccggcctg       720
cacgcgttct ttgaaagcag tcgaggggggc gctaggtgtg ggcagggacg agctggcgcg      780
gcgtcgctgg gtgcaccgcg accacgggca gagccacgcg gcgggaggac tacaactccc      840
ggcacacccc gcgccgcccc gcctctactc ccagaaggcc gcgggggggtg gaccgcctaa      900 gagggcgtgc gctcccgaca tgcccgcgcg cgcgccatta accgccagat ttgaatcgcg      960
ggacccgttg gcagaggtgg cggcggcggc atgggtgccc cgacgttgcc cctgcctgg      1020 cagccctttc tcaaggacca ccgcatctct acattcaaga actggccctt cttggagggc     1080
tgcgcctgca ccccggagcg                                                 1100
```

<210> SEQ ID NO 3
<211> LENGTH: 54
<212> TYPE: DNA
<213> ORGANISM: Homo sapiens

<400> SEQUENCE: 3
gggcgtgcgc tcccgacatg ccccgcggcg cgccattaac ccgccagatt tgaa      54

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aggtggccgc ttcctcgtcg      20

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
cttctcaact tggtccagc      19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gggtcgcgct ggctcgttg      19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
atgcatttac gaaggagaca      20

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
atgagatacc atgggtgccc cgacg      25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9

```
                                            -continued ttaaggatcc ctgctcgatg gcacg                                                  25

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ctggccatag aaccagagaa gtga                                                   24

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
ccacctctgc caacgggtcc cgcg                                                   24

<210> SEQ ID NO 12
<211> LENGTH: 10
<212> TYPE: DNA
<213> ORGANISM: Artificial Sequence
<220> FEATURE:
<223> OTHER INFORMATION: synthetic sequence

<400> SEQUENCE: 12 rrrcwwgyyy                                                                   10

<210> SEQ ID NO 13
<211> LENGTH: 33
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (11)...(11)
<223> OTHER INFORMATION: n = 0 to 13 nucleotides of any sequence
<220> FEATURE:
<221> NAME/KEY: misc_feature
<222> LOCATION: (22)...(22)
<223> OTHER INFORMATION: n = 0 to 15 nucleotides of any sequence
<220> FEATURE:
<221> NAME/KEY: misc_feature
<222> LOCATION: (28)...(28)
<223> OTHER INFORMATION: n = 5 to 6 nucleotides of any sequence

<400> SEQUENCE: 13
rrrcwwgyyy nrrrcwwgyy ynsgcggntt gaa                                         33
```